US011672686B2

(12) United States Patent
Nathanson et al.

(10) Patent No.: US 11,672,686 B2
(45) Date of Patent: Jun. 13, 2023

(54) BRACE HINGE WITH TELESCOPING PAD

(71) Applicant: DJO, LLC, Vista, CA (US)

(72) Inventors: Jeremy Nathanson, Vista, CA (US); Isabel Simons, Oceanside, CA (US)

(73) Assignee: DJO, LLC, Carlsbad, CA (US)

(*) Notice: Subject to any disclaimer, the term of this patent is extended or adjusted under 35 U.S.C. 154(b) by 1235 days.

(21) Appl. No.: 15/629,448

(22) Filed: Jun. 21, 2017

(65) Prior Publication Data

US 2017/0367867 A1 Dec. 28, 2017

Related U.S. Application Data

(60) Provisional application No. 62/354,553, filed on Jun. 24, 2016.

(51) Int. Cl.
*A61F 5/01* (2006.01)
*E05D 7/00* (2006.01)
(Continued)

(52) U.S. Cl.
CPC .............. *A61F 5/0123* (2013.01); *E05D 3/06* (2013.01); *E05D 7/0054* (2013.01);
(Continued)

(58) Field of Classification Search
CPC ........ A61F 5/01; A61F 5/0102; A61F 5/0123; A61F 5/0111; A61F 5/0118; A61F 5/0125; A61F 5/0127; A61F 5/013; A61F 2005/0134; A61F 2005/0137; A61F 2005/0139; A61F 2005/0141;
(Continued)

(56) References Cited

U.S. PATENT DOCUMENTS 4,520,804 A 6/1985 DiGeorge
5,586,970 A 12/1996 Morris et al.
(Continued)

FOREIGN PATENT DOCUMENTS

EP 1 829 507 9/2007

OTHER PUBLICATIONS

International Search Report and Written Opinion dated Dec. 12, 2017 in patent application No. PCT/US2017/038706.
(Continued)

*Primary Examiner* — Ophelia A Hawthorne
*Assistant Examiner* — Michael Milo
(74) *Attorney, Agent, or Firm* — Knobbe, Martens, Olson & Bear LLP

(57) ABSTRACT

A hinge which can be included on a brace is disclosed. The hinge can include a first arm, a second arm, and a hinge plate. The first and second arms can be connected to the hinge plate for rotation about first and second axes, respectively. The hinge plate can include an internally threaded aperture. The hinge can also include a force application assembly and an adjustment assembly. The adjustment assembly can include an externally threaded lead screw engaged with the internally threaded aperture, and having a medial end connected to the force application assembly and a keyed bore. The adjustment assembly can include a drive key having a keyed shaft slidingly engaged with the keyed bore and a knob connected to the drive key such that rotation of the knob causes displacement of the force application assembly.

13 Claims, 21 Drawing Sheets

(51) Int. Cl.
*E05D 3/06* (2006.01)
*E05D 11/00* (2006.01)

(52) U.S. Cl.
CPC .. *E05D 11/0054* (2013.01); *A61F 2005/0139* (2013.01); *A61F 2005/0165* (2013.01); *A61F 2005/0167* (2013.01); *A61F 2005/0172* (2013.01); *A61F 2005/0174* (2013.01); *A61F 2005/0181* (2013.01)

(58) Field of Classification Search
CPC ...... A61F 2005/0144; A61F 2005/0146; A61F 2005/0148; A61F 2005/0151; A61F 2005/0153; A61F 2005/0155; A61F 2005/0158; A61F 2005/0167; A61F 2005/0172; A61F 2005/0174; A61F 2005/0176; A61F 2005/0181; E05D 3/00; E05D 3/06; E05D 7/0054; E05D 11/0054
See application file for complete search history.

(56) References Cited

U.S. PATENT DOCUMENTS

| | | | |
|---|---|---|---|
| 5,807,294 A | | 9/1998 | Cawley et al. |
| 6,001,075 A * | | 12/1999 | Clemens ............... A61F 5/0123 602/26 |
| 6,413,232 B1 | | 7/2002 | Townsend et al. |
| 6,540,709 B1 | | 4/2003 | Smits et al. |
| 6,752,775 B2 | | 6/2004 | Seligman et al. |
| 6,960,175 B1 | | 11/2005 | Myers |
| 7,485,103 B2 | | 2/2009 | Mason |
| 8,419,669 B2 * | | 4/2013 | Bejarano ............... A61F 5/0125 602/16 |
| 8,690,812 B2 | | 4/2014 | Moir et al. |
| 2003/0015856 A1 | | 8/2003 | Seligman et al. |
| 2003/0153856 A1 * | | 8/2003 | Seligman ............... A61F 5/0123 602/26 |
| 2004/0267176 A1 * | | 12/2004 | Houser ............... A61F 5/0123 602/16 |
| 2007/0244419 A1 | | 10/2007 | Mason et al. |
| 2010/0010409 A1 * | | 1/2010 | Bejarano ............... A61F 5/0125 602/26 |
| 2010/0022929 A1 * | | 1/2010 | Pansiera ............... A61F 5/0123 602/16 |
| 2011/0034843 A1 | | 2/2011 | Seligman et al. |
| 2011/0071450 A1 * | | 3/2011 | Chiang ............... A61F 5/0123 602/16 |
| 2015/0038889 A1 * | | 2/2015 | Mason ............... A61B 17/132 24/68 D |

OTHER PUBLICATIONS

Fusion OA Brace Product Information, Top Shelf Orthopedics, Product brochure.
Rizzone, K et al., Using Casts, Splints, and Braces in the Emergency Department, Clinical Pediatric Emergency Medicine; 14(4): 340-348, Publication Date: 2013.
Telescoping Cool ROM Knee Brace Knee Support Ligament ACL MCL LCL PCL Injury Rehab, Source: http://www.alibaba.com/product-detail/Telescoping-Cool-ROM-Knee-Brace-Knee_60294517826.html, Date Accessed: Oct. 16, 2015. Date printed: Jun. 21, 2017.
Provectus hinged telescopic knee brace support blue and yellow dial Source: http://www.amazon.co.uk/Provectus-Hinged-Telescopic-Support-yellow/dp/B00N3WN1JO, Date Accessed: Oct. 26, 2015. Date printed: Jun. 21, 2017.

* cited by examiner

BRACE HINGE WITH TELESCOPING PAD

INCORPORATION BY REFERENCE TO ANY PRIORITY APPLICATIONS

This application claims priority to U.S. Provisional Application No. 62/354,553, filed Jun. 24, 2016, which is incorporated herein by reference in its entirety and for all purposes. U.S. application Ser. No. 10/074,520, filed Feb. 11, 2002, which issued as U.S. Pat. No. 6,752,775 on Jun. 22, 2004, and is also incorporated herein by reference in its entirety and for all purposes. Any and all applications for which a foreign or domestic priority claim is identified in the Application Data Sheet as filed with the present application are hereby incorporated by reference under 37 CFR 1.57.

BACKGROUND

The present invention relates to braces, such as orthopedic braces. More particularly, the present application describes a brace with a hinge having a pad that is adjustable to apply pressure toward and/or away from a joint. In some embodiments, the brace is a knee brace configured for treatment of osteoarthritis.

Osteoarthritis is a degenerative disease that can destabilize a knee joint. The disease commonly results from aging, joint overuse, or injury. A person afflicted with osteoarthritis may suffer chronic pain when his or her knee joint is statically or dynamically loaded that may be caused by an unbalanced loading on the joint. The unbalanced loading often collapses a compartment between the condyles of the femur and tibia, causing the condyles to contact each another. The contacting condyles may develop painful abrasions.

SUMMARY

In a first aspect, a hinge is disclosed. The hinge includes a first arm, a second arm, and a hinge plate. The first arm is connected to the hinge plate for rotation about a first axis and the second arm is connected to the hinge plate for rotation about a second axis. The hinge plate includes an internally threaded aperture. The hinge also includes a force application assembly and an adjustment assembly. The adjustment assembly includes an externally threaded lead screw engaged with the internally threaded aperture of the hinge plate. The lead screw includes a medial end connected to the force application assembly and a keyed bore extending along a longitudinal axis of the lead screw from a lateral end of the lead screw toward the medial end. The adjustment assembly also includes a drive key having a keyed shaft slidingly engaged with the keyed bore and a knob connected to a lateral end of the drive key such that rotation of the knob causes lateral or medial displacement of the force application assembly. The hinge may be used in a brace. The brace may be a knee brace. The hinge and the brace may be used for the treatment of osteoarthritis.

In some embodiments, the adjustment assembly further includes: a dial gear comprising a plurality of notches, and a tooth extending from the knob that engages with the plurality of notches during at least a portion of a full rotation of the knob such that rotation of the knob causes rotation of the dial gear. In some embodiments, the adjustment assembly further includes a pawl having a free end that engages with the plurality of notches of the dial gear. In some embodiments, the pawl is configured to prevent rotation of the dial gear when the tooth of the knob and the notches of the dial gear are not engaged. In some embodiments, the pawl comprises a C-shape that surrounds a portion of the dial gear. In some embodiments, the dial gear is configured to limit rotation of the knob. In some embodiments, the dial gear comprises a missing notch that limits rotation of the knob.

In some embodiments, the hinge further includes a plurality of position indicators on the dial gear, one of the plurality of position indicators viewable through a window in a cover of the hinge depending on a rotational position of the dial gear, the position indicators indicative of the lateral or medial displacement of the force application assembly. In some embodiments, a distance between the knob and dial gear is fixed. In some embodiments, rotation of the knob causes lateral or medial displacement of the externally threaded lead screw through the internally threaded aperture of the hinge plate. In some embodiments, the keyed bore of the lead screw comprises a D-bore shape and the keyed shaft of the drive key comprises a D-bore shape.

In some embodiments, the force application assembly includes a loading plate connected to the medial end of the lead screw, and a condyle shell. In some embodiments, the hinge includes a spacer between the force application assembly and the hinge plate. In some embodiments, the lead screw extends through an aperture in the spacer. In some embodiments, the spacer comprises foam. In some embodiments the hinge plate comprises a medial hinge plate, the hinge further including a lateral hinge plate, the first and second arms positioned between the lateral hinge plate and the medial hinge plate, and a cover, wherein the knob and dial gear are positioned between the cover and the lateral hinge plate. In some embodiments, a boss extends from an interior surface of the cover, and wherein the dial gear is mounted on and rotates around the boss. In some embodiments, the shaft of the drive key extends through an aperture in the lateral hinge plate.

In a second aspect, a hinge for a brace is disclosed. The hinge includes a medial hinge plate including an internally threaded anterior aperture having an anterior axis extending therethrough and an internally threaded posterior aperture having a posterior axis extending therethrough. The hinge includes a force application assembly. The hinge includes an anterior adjustment assembly aligned along the anterior axis and a posterior adjustment assembly aligned along the posterior axis. Each of the anterior and posterior adjustment assemblies include an externally threaded lead screw engaged with the internally threaded anterior aperture or the internally threaded posterior aperture of the medial hinge plate and having a medial end connected to the force application assembly and a keyed bore extending along a longitudinal axis of the lead screw from a lateral end of the lead screw toward the medial end. Each of the anterior and posterior adjustment assemblies include a drive key having a keyed shaft slidingly engaged with the keyed bore and a knob connected to a lateral end of the drive key such that rotation of the knob causes lateral or medial displacement of the force application assembly.

In some embodiments, the anterior adjustment assembly and the posterior adjustment assembly are independently adjustable. In some embodiments, the internally threaded anterior aperture and the internally threaded posterior aperture are aligned along a central transverse axis of the medial hinge plate.

In some embodiments, the hinge further includes an anterior adjustment indicator assembly associated with the anterior adjustment assembly and a posterior adjustment indicator assembly associated with the posterior adjustment assembly. In some embodiments, each of the anterior adjustment indicator assembly and the posterior adjustment indicator assembly include a dial gear comprising a plurality of notches, and a tooth extending from the knob that engages with the plurality of notches during at least a portion of a full rotation of the knob such that rotation of the knob causes rotation of the dial gear. In some embodiments, the adjustment assembly further includes a pawl having a free end that engages with the plurality of notches of the dial gear. In some embodiments, the pawl is configured to prevent rotation of the dial gear when the tooth of the knob and the notches of the dial gear are not engaged.

In some embodiments, the hinge includes a cover. The cover may include a circular anterior boss extending from an interior surface of the cover and a circular posterior boss extending from an interior surface of the cover. The dial gears may be mounted on and rotate around the bosses. In some embodiments, the anterior axis extends through the anterior boss and the posterior axis extends through the posterior boss. In some embodiments, the anterior boss is offset from a center longitudinal axis of the cover toward an anterior side of the hinge and the posterior boss is offset from the center longitudinal axis of the cover toward a posterior side of the hinge.

These and other aspects of the disclosure will become apparent from the following detailed description, drawings, and appended claims.

BRIEF DESCRIPTION OF THE DRAWINGS

The features and advantages of the brace and hinge described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

DETAILED DESCRIPTION

The following discussion presents detailed descriptions of the several embodiments of a brace and brace hinge with a telescoping force application as shown in the figures. These embodiments are not intended to be limiting, and modifications, variations, combinations, etc., are possible and within the scope of this disclosure.

Figure 1A:
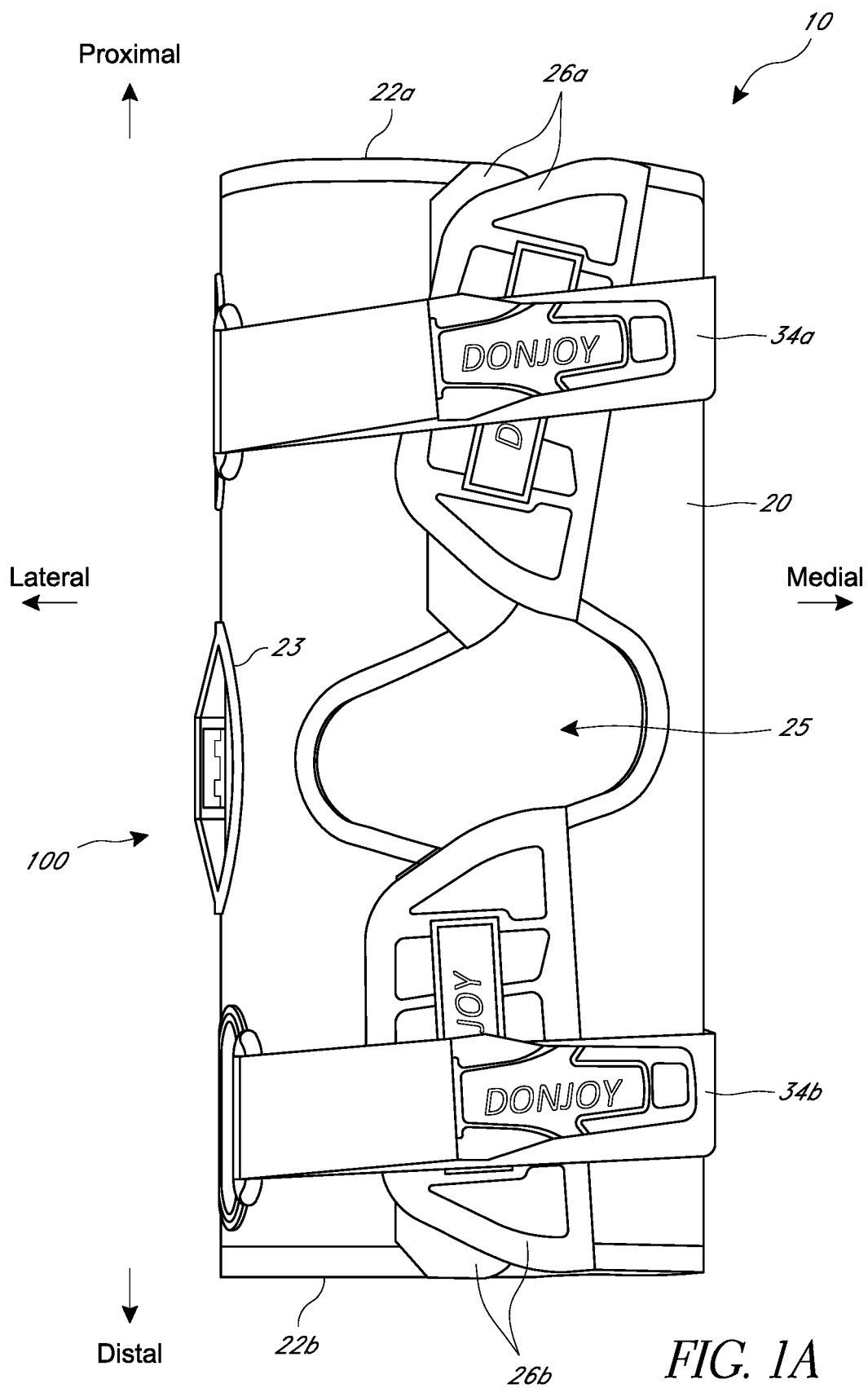
FIG. 1A shows an anterior view of one embodiment of a brace including a hinge with a telescoping force application assembly.
Figure 2A:
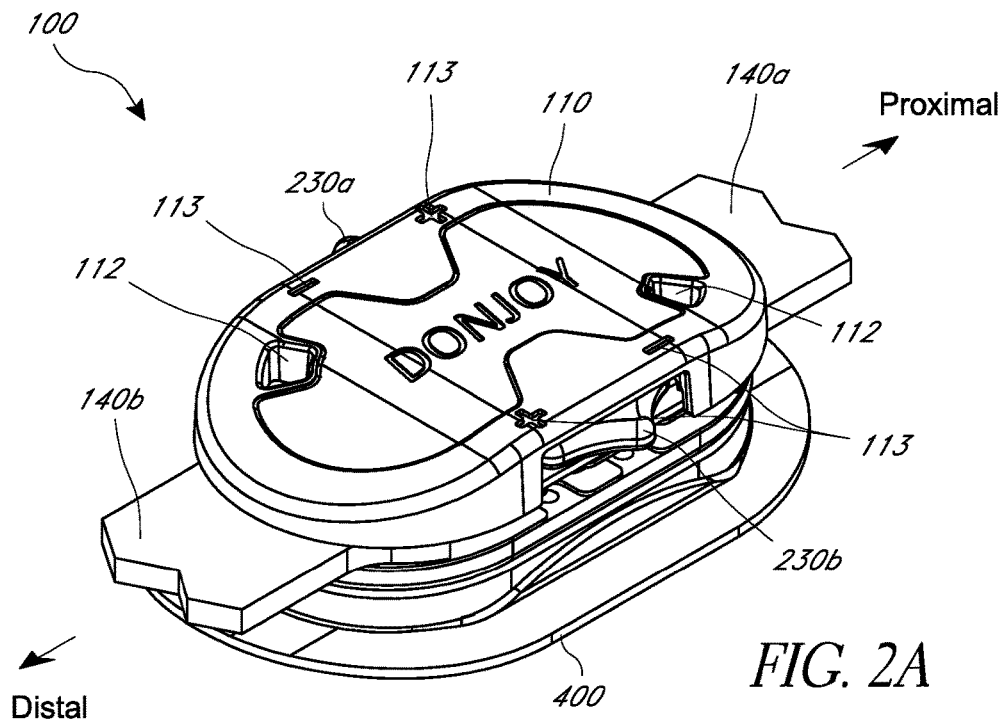
FIGS. 2A and 2B are perspective and lateral side views, respectively, of the hinge of FIG. 1A.

FIG. 1A shows an anterior view of one embodiment of a brace 10 including a hinge 100 with a telescoping force application assembly (the telescoping force assembly 400 is shown, for example, in FIG. 2A). The brace 10 can be used for the treatment of osteoarthritis of a knee. In some embodiments, the brace 10 is worn on the affected leg and is configured to apply a lateral/medial force to a lateral or medial side of the knee in order to unload the affected compartment of the knee joint and eliminate contact between the femur and tibia. In some embodiments, the force is applied to the knee at a point about 10° to 15° posterior of the normal axis of rotation of the knee, although other locations for the application of the force are possible.

In the illustrated embodiment, the hinge 100 is positioned on the lateral side of the brace 10 and is configured to provide a lateral/medial force to a lateral (outside) portion of a user's knee. Thus, the illustrated brace 10 is configured for use on a user's right leg, although the brace may be configured in a mirrored configuration for use on a user's left leg. Additionally, the brace 10 may be configured to provide a lateral/medial force to a medial (inside) portion of a user's knee. Accordingly, in some embodiments, the hinge 100 may be positioned on the medial side of the brace 10. In some embodiments, the brace 10 may be configured to apply a force on both the lateral and medial portions of a user's knee by, for example, including a hinge 100 on both the lateral and medial sides of the brace 10. Finally, while the illustrated brace 10 is configured to provide treatment for a knee joint, the brace 10 may be modified for use on other joints, such as, for example, elbows, ankles, or others.

The hinge 100 will be described below in detail in reference to FIGS. 2A-15. For ease of description, the hinge 100 illustrated in the figures will be described below as configured for use on a lateral side of a right knee. Those of skill in the art, however, will appreciate the hinge 100 may be adapted for use on the left side of a right knee, the right or left sides of a left knee, or on other joints in the body. While described as configured for use on a lateral side of a right knee, this application is not intended to be limited to only the described application.

Figure 1B:
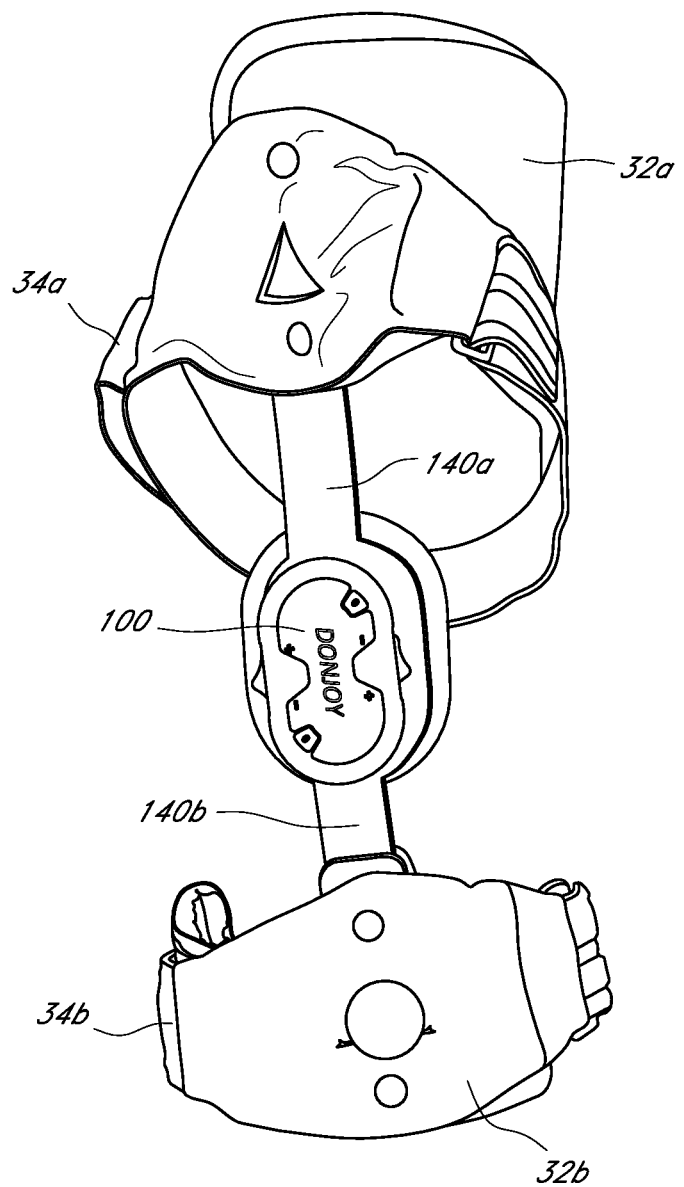
FIGS. 1B and 1C show lateral and medial views of an embodiment of a brace frame of the brace of FIG. 1A.
Figure 1C:
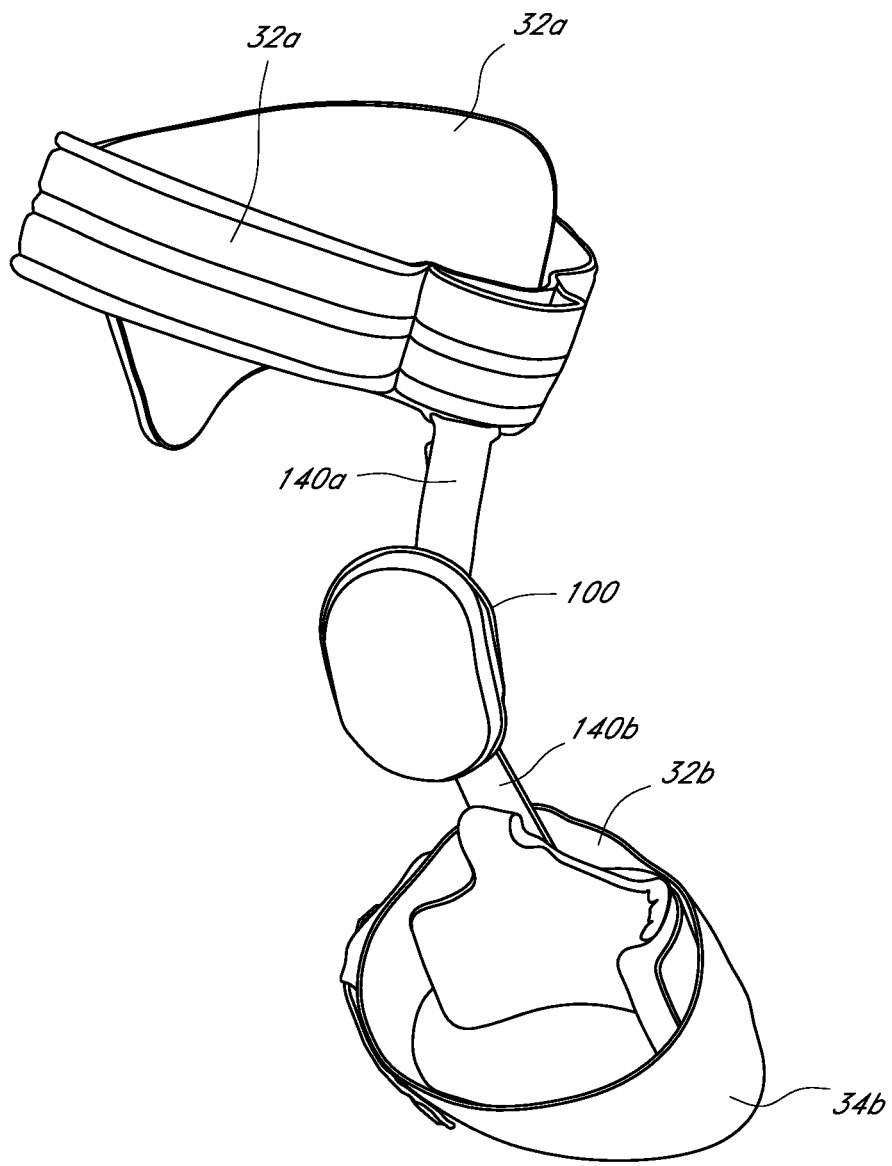

In the illustrated embodiment, the brace 10 includes a cover 20. The cover 20 may be configured to wrap around a user's leg. The hinge 100 may extend through an opening 23 in the cover 20. As illustrated, the cover 20 also includes a proximal opening 22a and a distal opening 22b. When the brace 10 is worn, the leg extends through the cover 20 from the proximal opening 22a to the distal opening 22b. The cover 20 also includes an anterior opening 25. The anterior opening 25 may be centered over the user's knee when the brace 10 is worn. In some embodiments, the cover 20 also includes a posterior opening. The cover 20 may be secured to the leg with one or more fasteners. For example, in the illustrated embodiment, the cover 20 includes proximal and distal fasteners 26a, 26b that close the cover 20 around the leg. The proximal and distal fasteners 26a, 26b may be hook and loop fasteners, as illustrated, or any other type of fastener including ties, buttons, zippers, toggles, etc. In the illustrated embodiment, proximal and distal tightening straps 34a, 34b extend through the cover 20. The proximal and distal tightening straps 34a, 24b may be connected to a brace frame 30 (as shown in FIGS. 1B and 1C). The proximal and distal tightening straps 34a, 34b may be configured to allow the brace 10 to be tightened around the leg. The proximal and distal tightening straps 34a, 34b may be secured with hook and loop fasteners, as illustrated, or any other type of fastener. In some embodiments, the cover 20 is made from fabric or another flexible material. The cover 20 may fit around the brace frame 30 (shown in FIGS. 1B and 1C), which provides structural support for the brace 10.

FIGS. 1B and 1C show lateral and medial views of an embodiment of a brace frame 30 of the brace 10 of FIG. 1A. As shown, the brace frame 30 includes a proximal leg support 32a and a distal leg support 32b. The proximal leg support 32a is configured to be secured to a user's upper leg above the knee. In some embodiments, the proximal leg support 32a is a rigid, semi-rigid, or flexible plate shaped to fit to a user's upper leg or thigh. In some embodiments, the proximal leg support 32a wraps around an anterior portion of the user's leg. In some embodiments, the proximal leg support 32a wraps entirely around the user's leg. The proximal tightening strap 34a may be attached to the proximal leg support 32a to secure the proximal leg support 32a to the leg. Similarly, the distal leg support 32b is configured to be secured to a user's lower leg below the knee. In some embodiments, the distal leg support 32b is a rigid, semi-rigid, or flexible plate shaped to fit to a user's lower leg or calf. In some embodiments, the distal leg support 32b wraps around a posterior portion of the user's leg. In some embodiments, the distal leg support 32b wraps entirely around the user's leg. The distal tightening strap 34b may be attached to the distal leg support 32b to secure the proximal leg support 32b to the leg. The proximal leg support 32a is attached to the hinge 100 by a proximal arm 140a and the distal leg support 32b is attached to the hinge 100 by a distal arm 140b.

Figure 1D:
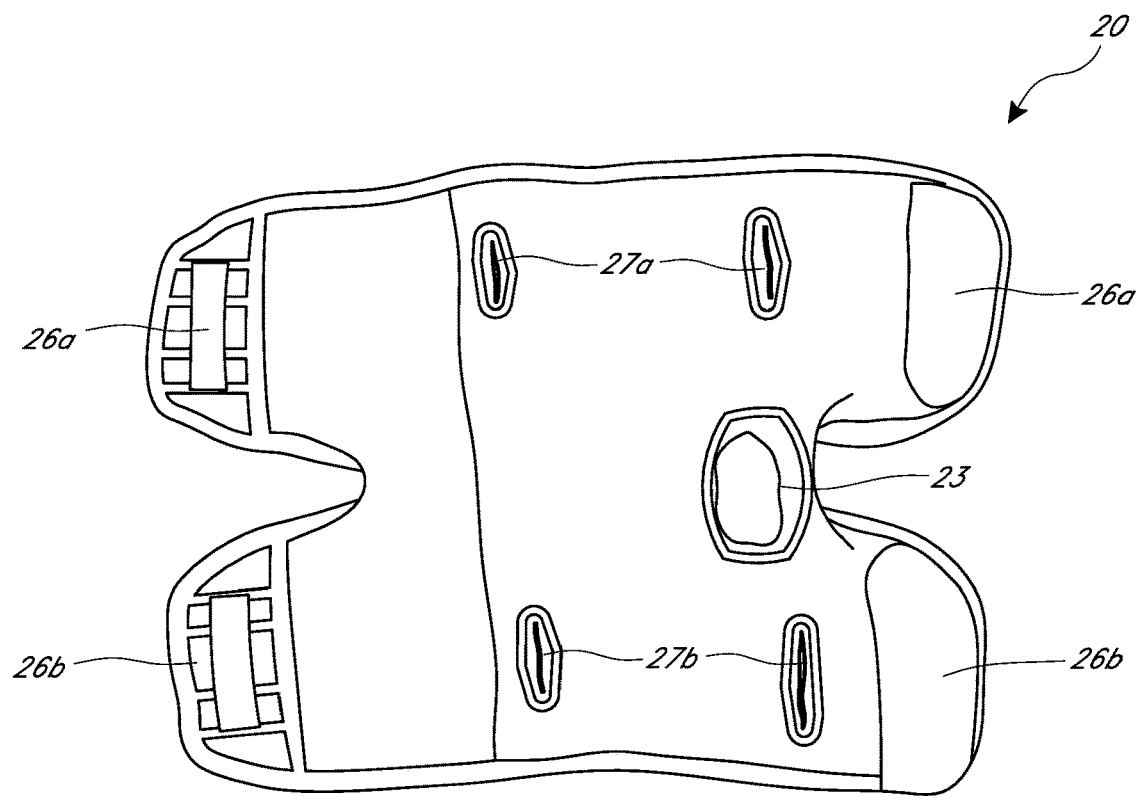
FIGS. 1D and 1E show outside and inside views of an embodiment to a cover of the brace of FIG. 1A.
Figure 1E:
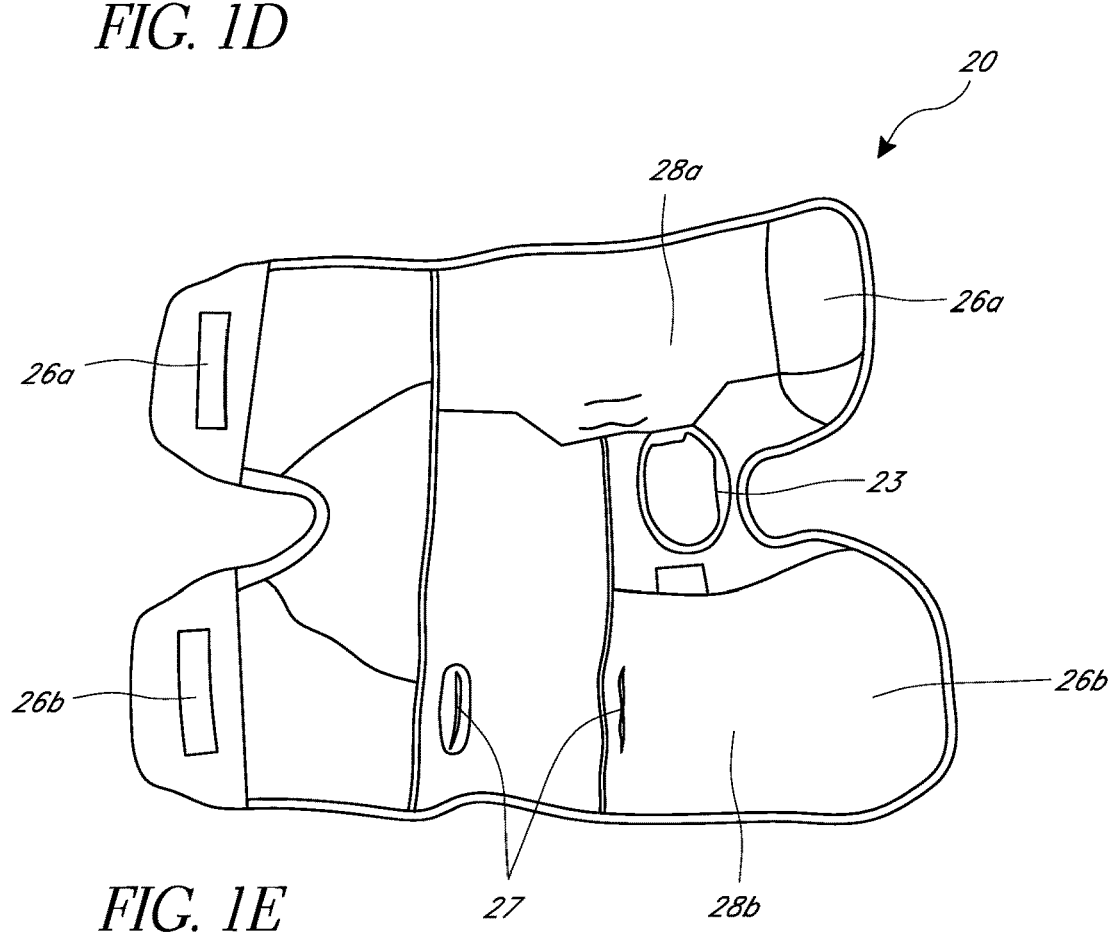

FIGS. 1D and 1E show outside and inside views of an embodiment to a cover 20 of the brace 10 of FIG. 1A (illustrated removed from the brace frame 30 of the brace 10). In the illustrated embodiment, the opening 23 for the hinge 100 is visible as well as several proximal and distal slits 27a, 27b configured to allow the proximal and distal tightening straps 34a, 34b to extend therethrough. As shown in the inside view of FIG. 1E, the cover 20 can include a proximal pocket 28a and a distal pocket 28b configured to receive the proximal and distal leg supports 32a, 32b. Other configurations for the cover 20 and the brace frame 30 are possible.

Figure 2B:
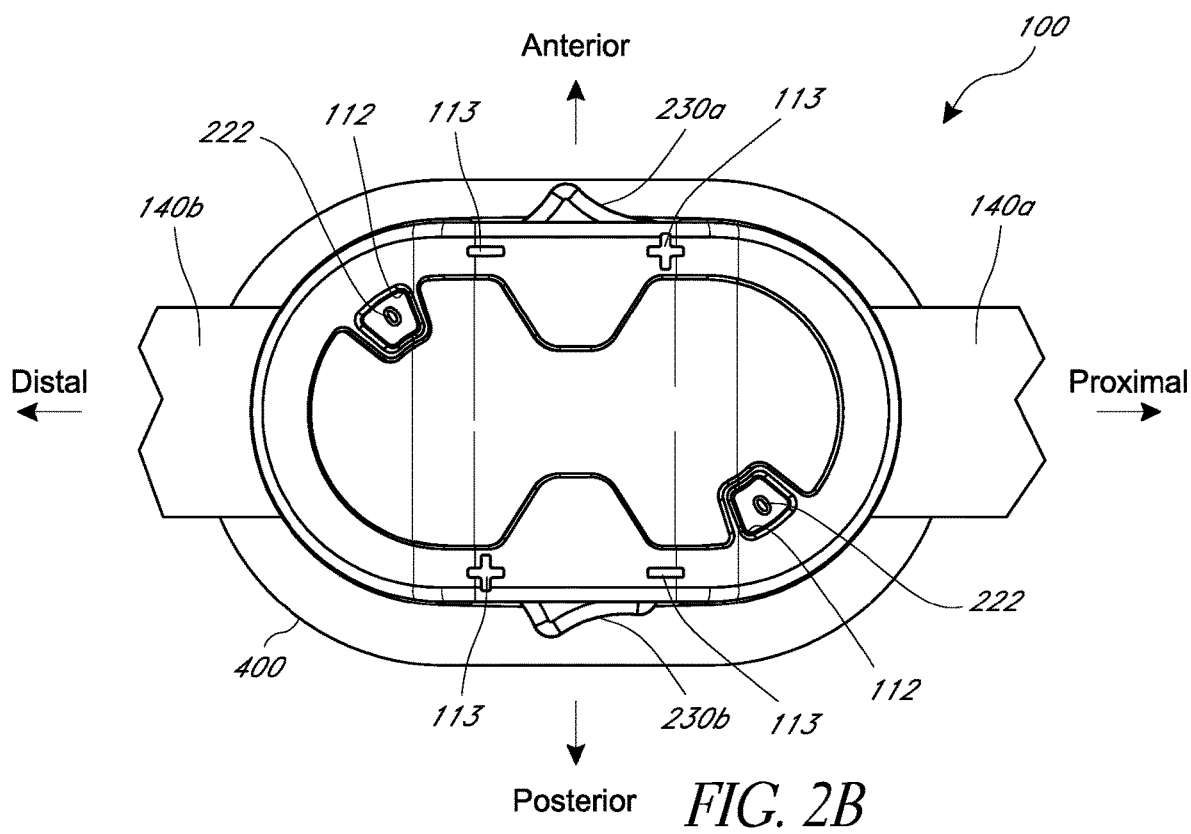

FIGS. 2A and 2B are perspective and lateral side views, respectively, of the hinge 100 of FIG. 1. As will become more fully apparent from the following description, the hinge 100 may be configured to apply a lateral/medial force to a user's knee and/or to allow, limit, or prohibit extension and flexion of the knee. In the illustrated embodiment, the hinge 100 includes a proximal arm 140a and a distal arm 140b. Only the portions of the proximal and distal arms 140a, 140b that are attached to the hinge 100 are illustrated. However, the opposite ends of the proximal and distal arms 140a, 140b (not shown in the figures) can be connected to other components of the brace 10 and/or secured to a user's leg. For example, in some embodiments, the proximal arm 140a extends proximally from the hinge 100 and is connected to a proximal portion of the brace 10 that is secured above the knee on a user's thigh. Similarly, in some embodiments, the distal arm 140b extends distally from the hinge 100 and is connected to a distal portion of the brace 10 that is secured below the knee on a user's lower leg.

In some embodiments, the proximal and distal arms 140a, 140b are pivotally connected to the hinge 100 (as will be described below in greater detail with reference to FIG. 6). For example, the proximal and distal arms 140a, 140b can be configured to rotate with respect to the hinge 100 or with respect to each other in response to the flexion and/or extension of the knee. In some embodiments, the proximal and distal arms 140a, 140b are configured to rotate independently. In some embodiments, the proximal and distal arms 140a, 140b are configured to rotate together. For example, rotation of the proximal arm 140a may be configured to cause a corresponding and equal rotation of the distal arm 140b, or vice versa. In some embodiments, the rotation of the proximal and distal arms 140a, 140b lies in a single plane, although this need not be the case in all embodiments. In some embodiments, the hinge 100 may be bicentric. That is, the hinge 100 may comprise two axes of rotation, one for each of the proximal and distal arms 140a, 140b. The two axes may be spaced apart to produce a hinge rotation that approximates the bending dynamics of the human knee. In some embodiments, the hinge 100 may be monocentric. That is, the proximal and distal arms 140a, 140b may share a common axis of rotation.

In some embodiments, the proximal and distal arms 140a, 140b can be locked in place, such that they do not rotate. In some embodiments, the hinge 100 can be configured such that the rotation of the proximal and distal arms 140a. 140b can be limited. In this way, the brace 10 can be configured to provide a limited range of motion.

The hinge 100 also includes a force application assembly 400. The force application assembly 400 is configured to apply a lateral/medial force to a user's knee. As will be described in greater detail below, the force application assembly 400 can be displaced in a lateral/medial direction to apply the lateral/medial force. In some embodiments, the brace and hinge 100 are configured such that the force application assembly 400 is positioned over a lateral or medial side of a user's knee when the brace is worn. Thus, the force application assembly 400 can be configured to apply the lateral/medial force to the lateral or medial side of a user's knee.

The hinge 100 is configured such that the force applied by the force application assembly 400 can be adjusted. In the illustrated embodiment, the hinge 100 includes an anterior actuator or knob 230a and a posterior actuator or knob 230b. The anterior and posterior knobs 230a, 230b may be manipulated, operated, or adjusted to control the displacement of the force application assembly 400. In the illustrated embodiment, the anterior knob 230a extends out an anterior knob opening 116a in a cover 110 of the hinge 100 and the posterior knob 230b extends out a posterior knob opening 116b in the cover 110. While an anterior and a posterior knob 230a, 230b are illustrated in the figures and described throughout this application, in some embodiments, the hinge 100 may be configured with the knobs (or other actuators) in other positions. For example, both knobs could be positioned on the anterior side or the posterior side of the hinge, or, as another example, the knobs could extend out a lateral surface of the cover 110. Further, while two knobs are illustrated and described, in some embodiments, the hinge 100 may include only a single knob or more than two knobs.

In the illustrated embodiment, the cover 110 includes windows 112 through which position indicators 222 are visible. As the anterior and posterior knobs 230a, 230b are adjusted the position indicators 222 visible through the windows 112 are changed to indicate the displacement of the force application assembly 400. In the illustrated embodiment, the position indicators 222 are numerical values, although other indicators, for example, colors, symbols, etc. are possible. In some embodiments, the windows 112 are configured as two apertures on opposite corners of the lateral surface of the cover 110, although other numbers of windows 112 and/or other placements of the windows 112 on the hinge 100 are possible. The cover 110 may also include additional indicators or markings 113 that can indicate the effect of rotation of the anterior or posterior knobs 230a, 230b in either the clockwise or counterclockwise directions. For example, as illustrated, the cover 110 includes "plus" and "minus" markings 113 indicating that rotation of the anterior or posterior knobs 230a, 230b in either the clockwise or counterclockwise directions will cause positive and negative displacement, respectively, of the force application assembly 400.

Figure 3A:
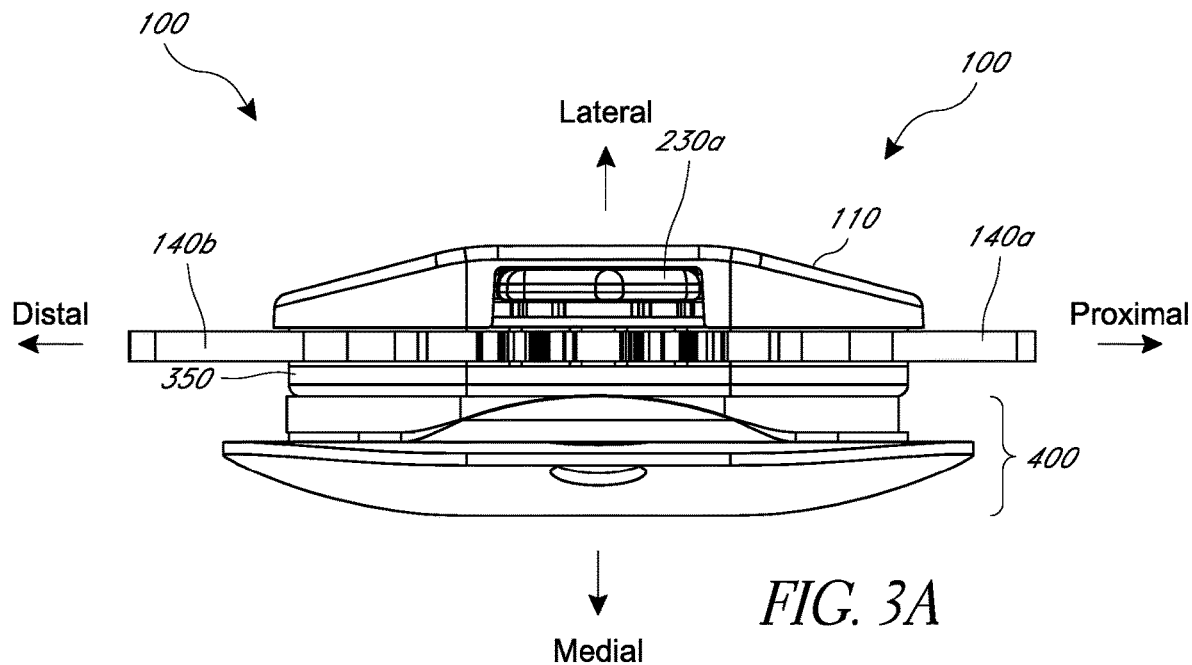
FIG. 3A shows an anterior view of the hinge of FIG. 2A with the force application assembly in a first position.

Example displacement of the force application assembly 400 will be described below in reference to FIGS. 3A through 4B. FIGS. 3A and 4A show anterior and top views of the hinge 100 with the force application 400 assembly in a first position. In the illustrated first position, the force application assembly 400 is positioned against a medial hinge plate 350 of the hinge 100. The first position may represent a retracted position or a position of approximately zero displacement. The first position may also represent application of a lower lateral/medial force as compared with a second position shown in FIGS. 3B and 4B, which may represent application of a higher lateral/medial force as compared with the first position. In some embodiments, the force application assembly 400 may apply approximately zero force to the knee in the first position.

Figure 3B:
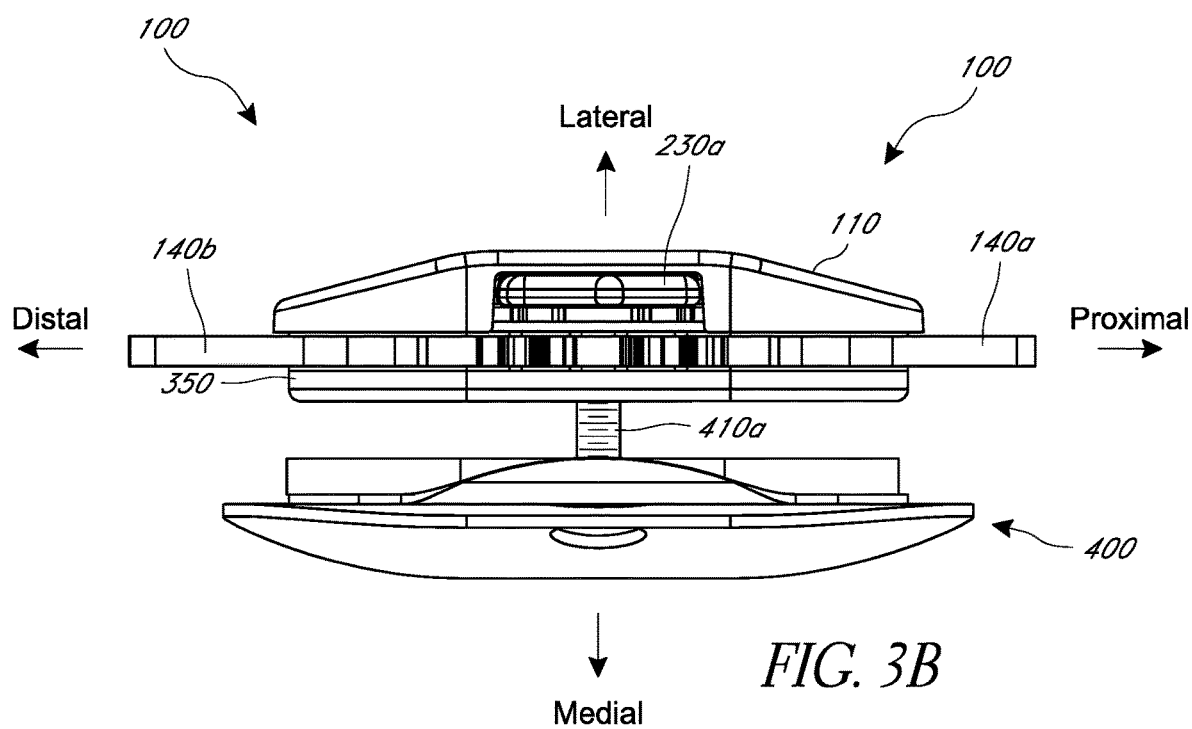
FIG. 3B is an anterior view of the hinge of FIG. 2A in a second configuration with the force application assembly extended in a medial/lateral direction.
Figure 4A:
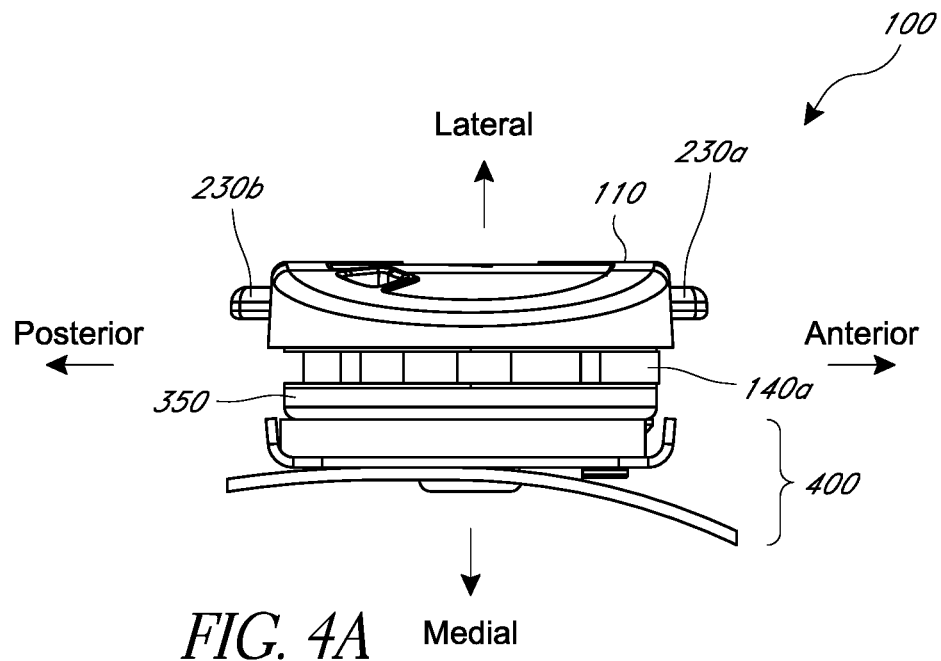
FIG. 4A shows a top view of the hinge of FIG. 2A with the force application assembly in the first position.
Figure 4B:
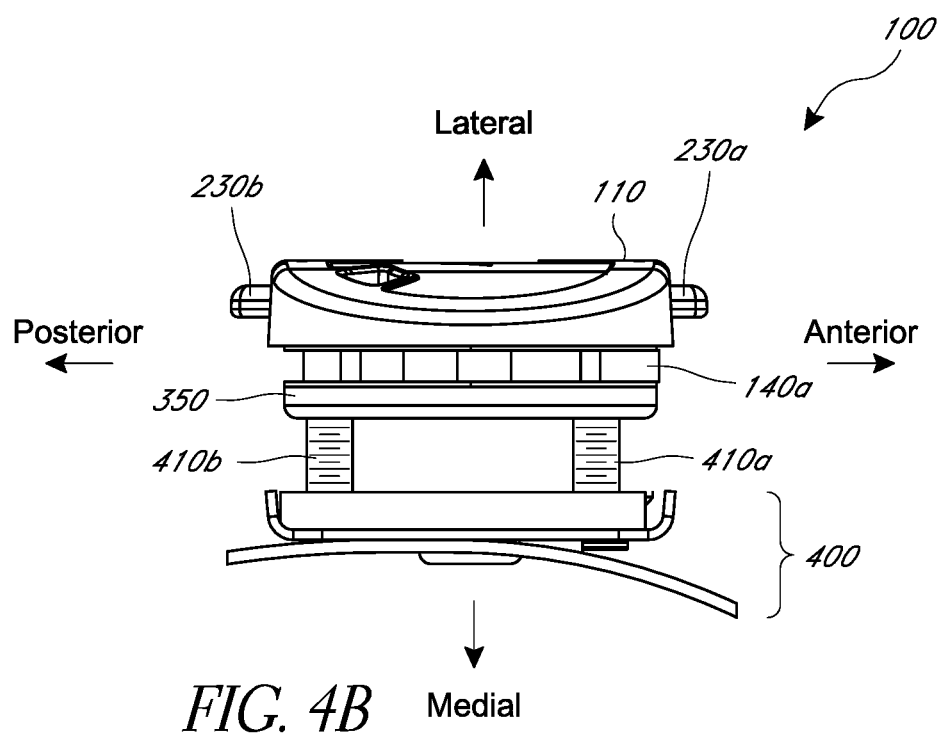
FIG. 4B is a top view of the hinge of FIG. 2A in the second configuration with the force application assembly extended in the medial/lateral direction.

FIGS. 3B and 4B show anterior and top views, respectively, of the hinge 100 with the force application 400 in a second configuration. The second configuration may represent an extended or displaced position relative to the medial hinge plate 350. In the second configuration, the force application assembly 400 has been displaced (in other words, extended) in a medial/lateral direction. In some embodiments the displacement is at predetermined displacement increment (e.g., 1 mm, 1.5 mm, 2 mm, 3 mm or any other predetermined increment). In some embodiments the displacement can be set to be any value between the least displacement and the greatest displacement that the force application assembly 400 can be positioned (for example, configured for a non-incremental displacement). In some embodiments, the force application assembly 400 can be displaced at positions from between about 0 mm and about 50 mm. In some embodiments, the maximum displacement of the force application assembly 400 (measured relative to the medial hinge plate 350) is approximately 30 mm, approximately 20 mm, or approximately 10 mm. The force application assembly 400 can be transitioned between the first position and the second position (and any position in between) by manipulation of the anterior and posterior knobs 230a, 230b. As will be described in greater detail below, displacement of the force application assembly 400 can be caused by the telescoping or extension of anterior and posterior lead screws 410a, 410b through the medial hinge plate 350. The anterior and posterior knobs 230a, 230b can be operatively connected to the lead screws 410a, 410b. In the anterior view of FIG. 3B, only the anterior lead screw 410a is visible as the posterior lead screw 410b is located behind the anterior lead screw 410a. FIG. 4B illustrates both the anterior lead screw 410a and the posterior lead screw 410b.

In some embodiments, the anterior and posterior lead screws 410a, 410b are independently adjustable, for example, via independent manipulation of the anterior and posterior knobs 230a, 230b. In the illustrated embodiments of FIGS. 3B and 4B, the anterior and posterior lead screws 410a, 410b have been adjusted evenly (that is, with equal amounts of extension through the medial hinge plate 350) such that the force application assembly 400 is displaced an equal anterior and posterior amount. Although not illustrated, the anterior and posterior lead screws 410a, 410b can be adjusted to provide an uneven force via the force application assembly 400. For example, if the anterior lead screw 410a is adjusted to provide a greater displacement than the posterior lead screw 410b, the force application assembly 400 will be positioned at an angle with respect to the medial hinge plate 350 and will apply a greater anterior force and a smaller posterior force. As another example, if the anterior lead screw 410a is adjusted to provide a smaller displacement than the posterior lead screw 410b, the force application assembly 400 will be positioned at an angle with respect to the medial hinge plate 350 such that a smaller anterior force and a greater posterior force is applied. Thus, in some embodiments, the hinge 100 is configured for independent adjustment of the force application assembly 400, allowing a user to apply varying and differing pressure to the anterior and posterior portions of the knee.

Further, while the illustrated embodiment includes an anterior and a posterior lead screw 410a, 410b, other arrangements are possible. For example, the hinge 100 can include a proximal and a distal lead screw allowing for independent adjustment in a proximal/distal direction. In some embodiments, the hinge 100 can include a single lead screw.

Figure 5A:
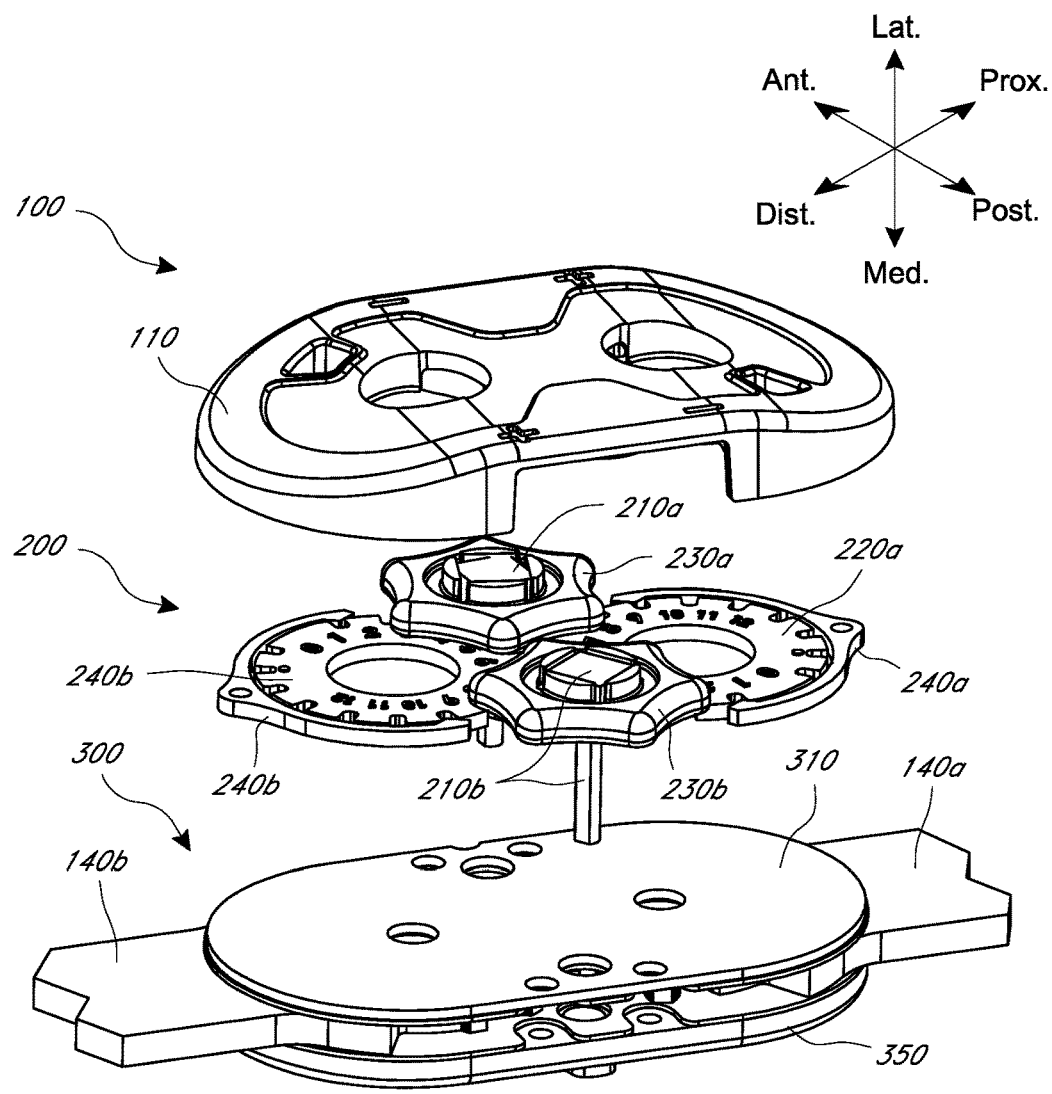
FIGS. 5A and 5B are lateral and medial partially exploded perspective views, respectively, of the hinge of FIG. 2A.
Figure 5A:
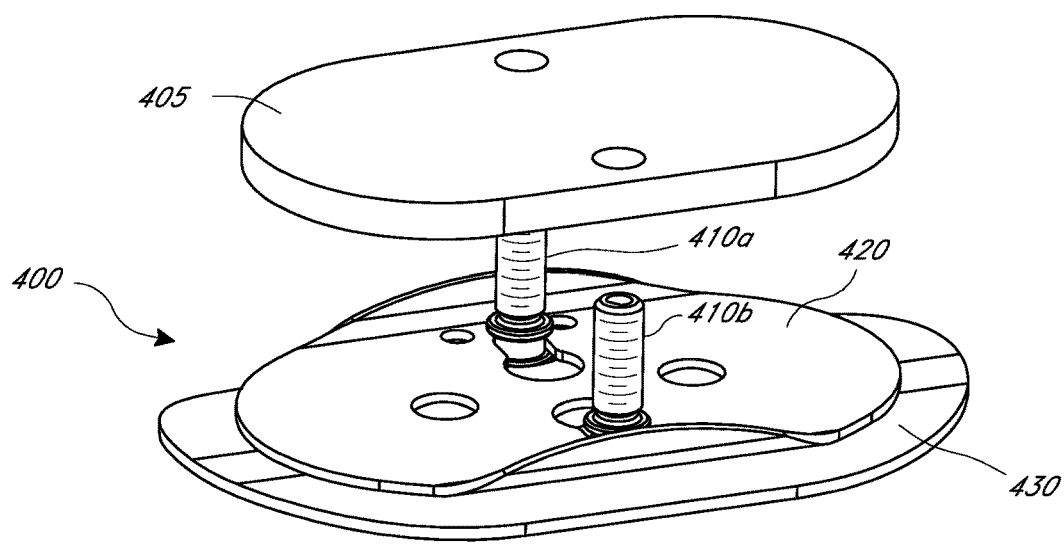
Figure 5B:
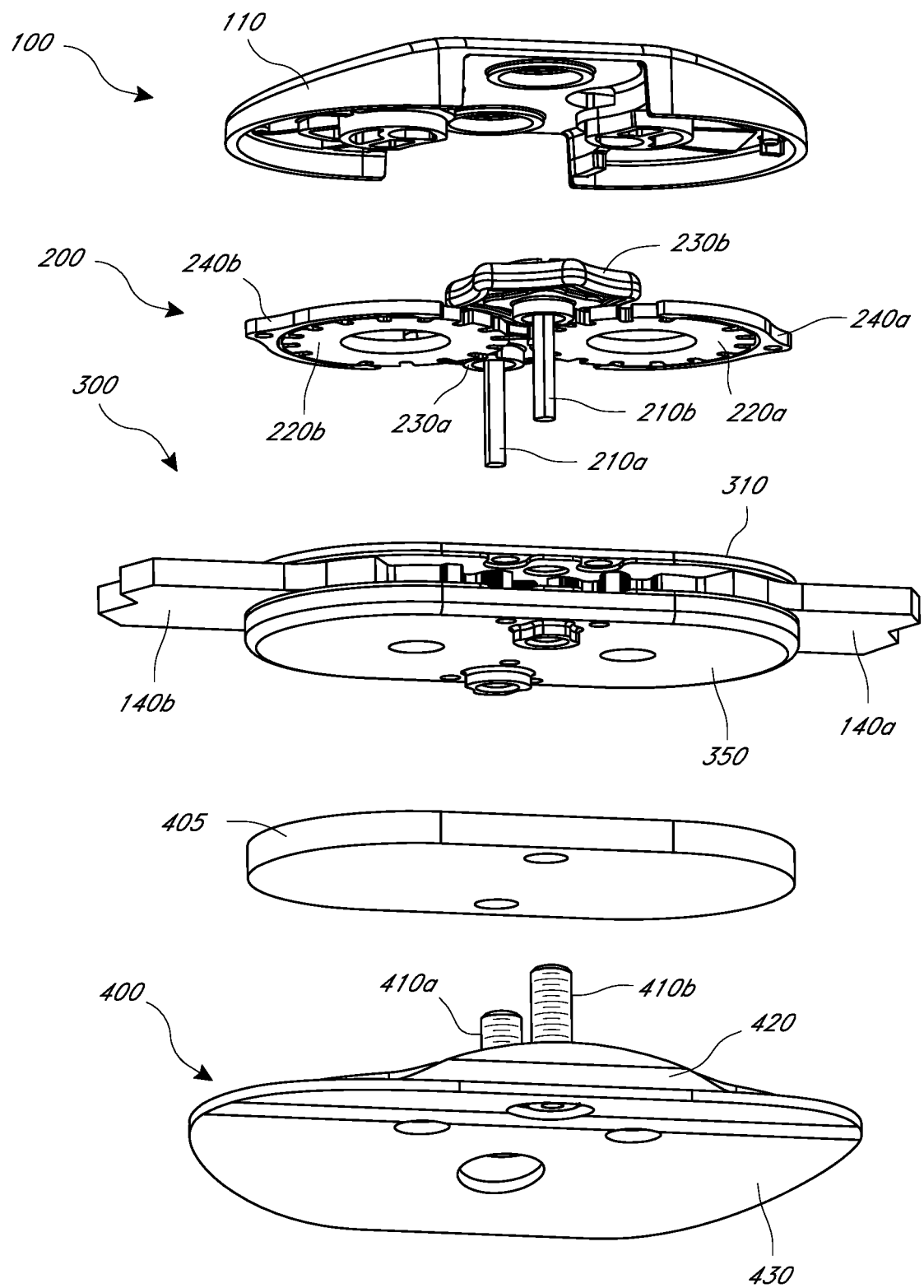

FIGS. 5A and 5B are lateral and medial partially exploded perspective views, respectively, of the hinge 100 and will be described concurrently. In the illustrated embodiment, the hinge 100 includes a hinge mechanism assembly 300, the force application assembly 400, an adjustment assembly 200, and the cover 110. Not all of these components are necessary in all embodiments of the hinge 100.

In the illustrated embodiment, the hinge mechanism assembly 300 includes a lateral hinge plate 310 and a medial hinge plate 350. End portions of the proximal and distal arms 140a, 140b are received between the lateral and medial hinge plates 310, 350. In some embodiments, the hinge mechanism assembly 300 is configured to allow the proximal and distal arms 140a, 140b to rotate as described above. The hinge mechanism assembly 300 will be described in detail below in reference to FIGS. 6 and 7.

The hinge 100 also includes the force application assembly 400. In the illustrated embodiment of FIGS. 5A and 5B, the force application assembly 400 includes a loading plate 420 and a condyle shell 430, as well as the anterior and posterior loading screws 410a, 410b. The force application assembly 400 is positioned below (in other words, on the medial side of) the medial hinge plate 350. The force application assembly 400 can include a foam (or other cushioning material) pad 405 positioned between the medial hinge plate 350 and the loading plate 420 as illustrated. As discussed previously, the force application assembly 400 is configured for lateral/medial displacement relative to the medial hinge plate 350. In some embodiments, one or more of these components may be omitted. The force application assembly 400 is described in detail below in reference to FIG. 10.

The hinge also includes an adjustment assembly 200. In the illustrated embodiment of FIGS. 5A and 5B, the adjustment assembly 200 includes an anterior drive key 210a, the anterior knob 230a, an anterior dial gear 220a, and an anterior pawl 240a that are configured to allow displacement of the anterior lead screw 410a through the medial hinge plate 350 to control lateral/medial displacement of an anterior portion of the force adjustment assembly 400. The adjustment assembly 200 also includes a posterior drive key 210b, the posterior knob 230b, a posterior dial gear 220b, and a posterior pawl 240b that are configured to allow displacement of the anterior lead screw 410a through the medial hinge plate 350 to control lateral/medial displacement of a posterior portion of the force adjustment assembly 400. The adjustment assembly is positioned between the lateral hinge plate 310 and the cover 110. Again, not all of these components are necessary in all embodiments of the hinge 100. The adjustment assembly 200 and cover 110 will be described in detail in reference to FIGS. 8A-9B.

Figure 6:
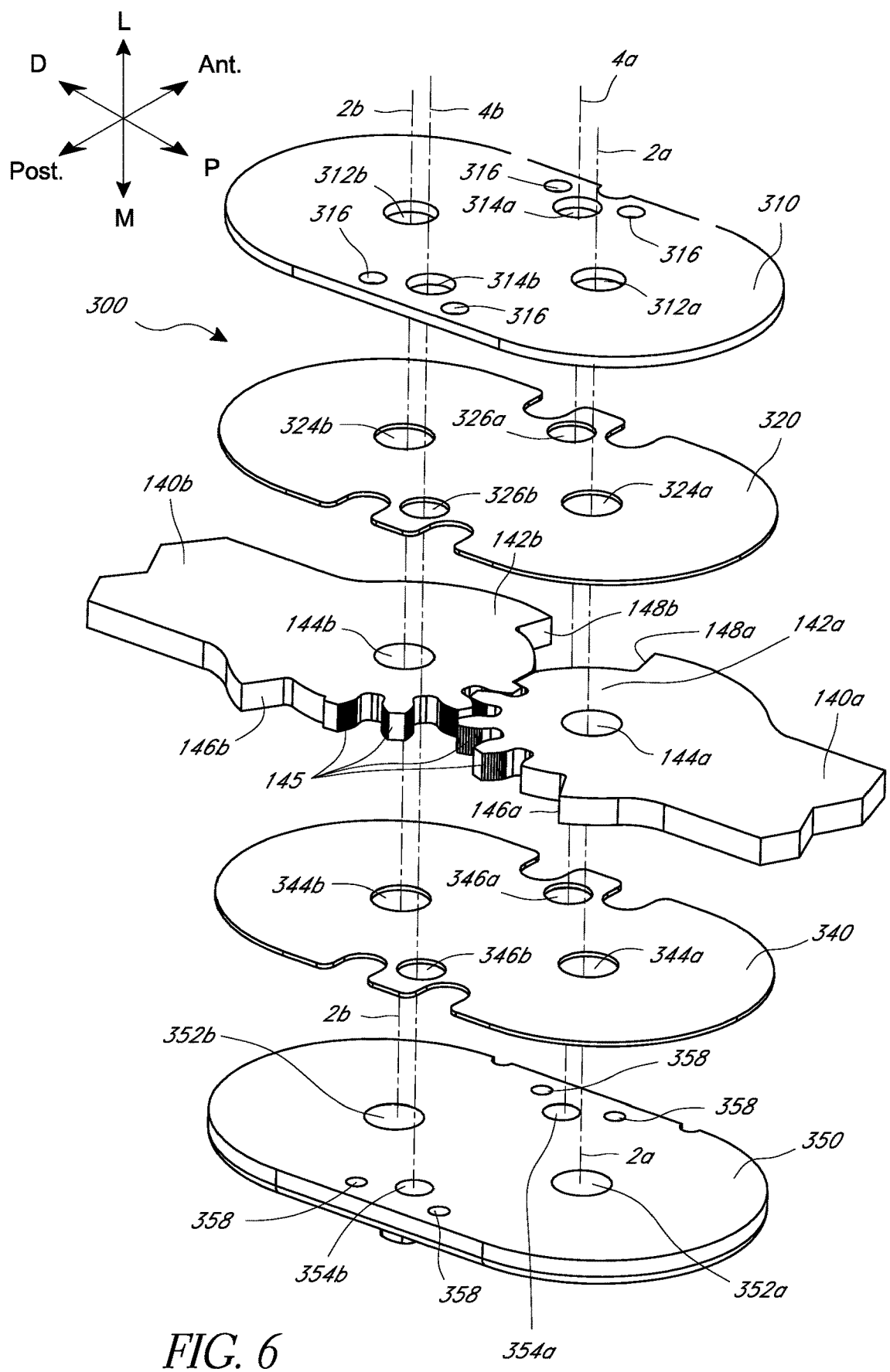
FIG. 6 is an exploded perspective view of an embodiment of a hinge assembly for the hinge of FIG. 2A.
Figure 7:
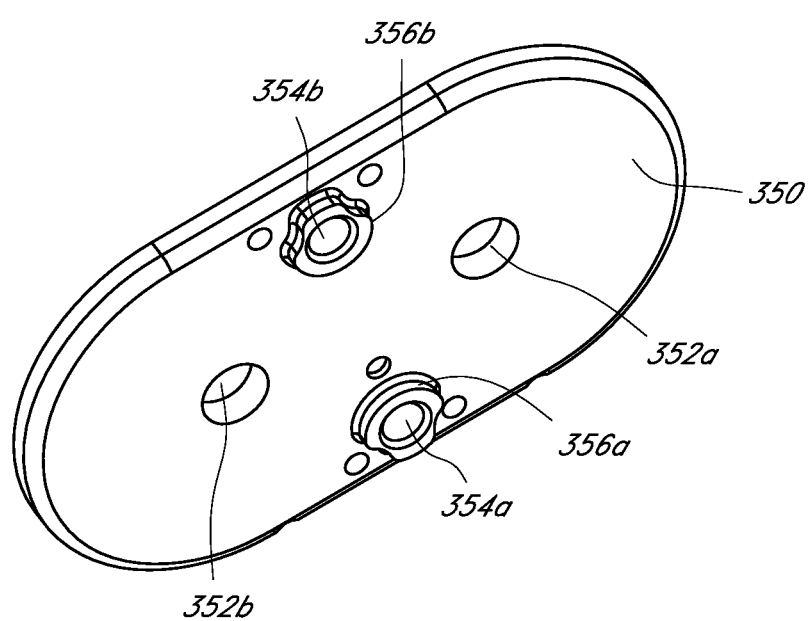
FIG. 7 shows a perspective view of the medial side of a hinge plate of the hinge of FIG. 2A.

FIG. 6 is an exploded view of one embodiment of the hinge mechanism assembly 300. In the illustrated embodiment, the hinge mechanism assembly 300 includes the lateral hinge plate 310 and the medial hinge plate 350. FIG. 7 shows the medial face of the medial hinge plate 350. As illustrated, each of the lateral and medial hinge plates 310, 350 is a flat bracket or plate and is substantially oval shaped, although other shapes are possible. In some embodiments, the profile shape of each of the lateral and medial hinge plates 310, 350 is the same. Each of the lateral and medial hinge plates 310, 350 can be between approximately 0.05 mm and 1 cm mm thick, although other thicknesses are possible. In some embodiments, the medial hinge plate 350 is thicker than the lateral hinge plate 310, although, in some embodiments, the medial hinge plate 350 and the lateral hinge plate 310 can have the same thickness or the lateral hinge plate 310 can be thicker than the medial hinge plate.

As illustrated, for some embodiments, each of the lateral and medial hinge plates 310, 350 includes a plurality apertures extending there through. In some embodiments, one or more of the apertures of the lateral hinge plate 310 are aligned with the one or more apertures of the medial hinge plate 350. In some embodiments, apertures are aligned along four distinct axes of the hinge mechanism assembly 300. For example, apertures can be aligned along a proximal arm rotation axis 2a, a distal arm rotation axis 2b, an anterior adjustment axis 4a, and a posterior adjustment axis 4b. In some embodiments, the proximal and distal arms 140a, 140b are configured to rotate around the proximal and distal arm rotation axes 2a, 2b. In some embodiments, displacement of the anterior and posterior lead screws 410a, 410b occurs along the anterior and posterior adjustment axes 4a, 4b, respectively.

The medial hinge plate 350 includes a proximal aperture 352a and distal aperture 352b. In some embodiments, the proximal and distal apertures are aligned along a central longitudinal axis of the medial hinge plate 350. In some embodiments, the proximal aperture 352a is located substantially in the center of a proximal half of the medial hinge plate 350, and the distal aperture 352b is located substantially in the center of a distal half of the medial hinge plate 350. The medial hinge plate 350 also includes an anterior aperture 354a and posterior aperture 354b. In some embodiments, the anterior aperture 354a and the posterior apertures 354b can be aligned along a central transverse axis of the medial hinge plate 350. In some embodiments, the anterior aperture 354a is located near a center of an anterior edge of the medial hinge plate 350, and each posterior aperture 354b is located near a center of a posterior edge of the medial hinge plate 350. The anterior and posterior apertures 354a, 354b can be internally threaded. As will be described below, in some embodiments, the internal threads of the anterior and posterior apertures 354a, 354b engage with external threads of the lead screws 410a, 410.

In the illustrated embodiment, the medial hinge plate 350 includes apertures 358. The apertures 358 are positioned near the anterior and posterior sides of the medial hinge plate and surround the anterior and posterior apertures 354a, 354b. In some embodiments, the additional apertures 358 are smaller than the anterior and posterior apertures 354a, 354b and/or the proximal and distal apertures 352a, 352b. While additional anterior and posterior apertures 358 are illustrated in the figures and described throughout this application, in some embodiments, the hinge mechanism assembly 300 may be configured without these apertures or with additional apertures in other positions. As shown in the FIG. 7, the medial face of the medial hinge plate 350 includes anterior and posterior bosses 356a, 356b surrounding the anterior and posterior apertures 354a, 354b. The anterior and posterior bosses 356a, 356b may extend the internally threaded length of the anterior and posterior apertures 354a, 354b. The anterior and posterior bosses 356a, 356b may also serve as a contact point for the force application assembly 400. In other words, in some embodiments, the force application assembly 400 can be retracted until it contacts the bosses 356a, 356b.

The lateral hinge plate 310 may include a plurality of apertures that correspond to the apertures of the medial hinge plate 350 described above. For example, in the illustrated embodiment, the lateral hinge plate includes a proximal aperture 312a, a distal aperture 312b, an anterior apertures 314a, and a posterior aperture 314b. In some embodiments, the anterior and posterior apertures 314a, 314b are not threaded. The lateral hinge plate 310 also includes additional apertures 316.

The anterior apertures 354a of the lateral and medial hinge plates 310, 350 are aligned along the anterior adjustment axis 4a. The posterior apertures 354b of the lateral hinge plates are aligned along the posterior adjustment axis 4b. While an anterior and posterior aperture 354a, 354b are illustrated in the figures and described throughout this application, in some embodiments, the hinge mechanism assembly 300 may be configured with the apertures in other positions. For example, both apertures could be located toward one side of the hinge plates or be spaced from a proximal/distal axis of the hinge plates. The anterior and posterior apertures 354a, 354b may include internal threads that cooperate with an anterior lead screw 410a and posterior lead screw 410b (not shown), respectively, to adjust an amount of pressure exerted on a lateral side of a user's knee.

The lateral and medial hinge plates 310, 350 may be made from metal, plastic, or other suitable materials. In some embodiments, the lateral and medial hinge plates 310, 350 are substantially rigid. In some embodiments, the lateral and medial hinge plates 310, 350 are flexible. In some embodiments, one of the lateral or medial hinge plates 310, 350 can be omitted.

The proximal and distal arms 140a, 140b are positioned between the lateral and medial hinge plates 310, 350. In some embodiments, the proximal arm 140a is formed from a substantially flat plate. The plate may be, for example, between approximately 0.5 mm and 2 cm thick, although other thicknesses are possible. The proximal arm 140a can include a hinge-engaging portion 142a at a posterior end, which has a complex perimeter, including an anterior shoulder 148a, a posterior shoulder 146a, and a plurality of gear teeth 145 along distal and posterior edges. The proximal arm 140a includes pivot aperture 144a near the proximal end. The distal arm 140b is substantially identical to the proximal arm 140a, but is a substantial mirror of the proximal arm 140a about an axis that passes through a center of the hinge 100 in an anterior/posterior direction. The proximal and distal arms 140a, 140b rotate around the proximal and distal arm rotation axes 2a, 2b about the respective pivot apertures 144a, 144b, such that the plurality of teeth gear of both arms engage each other. This causes rotation of one arm to be transferred to the other arm. In some embodiments, there is a limited plurality (i.e., a limited number) of gear teeth 144 between the anterior and posterior shoulders 148b, 146b of the proximal and distal arms 140a, 140b to limit the range of motion of brace 10. In another embodiment, the plurality of gear teeth of both arms may be configured to rotate together, at equal angles from an axis in the distal/proximal direction. In other embodiments, the proximal and distal arms 140a, 140b can be locked in place, such that they do not rotate. The proximal and distal arms 140a, 140b can be made from a metal, plastic, or other suitable materials. In some embodiments, the proximal and distal arms 140a, 140b are rigid. In some embodiments, the proximal and distal arms 140a, 140b are flexible.

In some embodiments, the hinge mechanism 300 can include a lateral plate, spacer, or washer 320 and a medial plate, spacer, or washer 340 on each of the lateral and medial sides of the proximal and distal arms 140a, 140b, for example as illustrated in FIG. 6. The lateral and medial washers 320, 340 can each be substantially similar to each other. The lateral washer 320 will now be described, but the description is also applicable to the medial washer 340. The lateral washer 320 may be configured as a thin, flat plate. The lateral washer 320 can include a plurality of apertures aligned with one or more of the apertures of the lateral and/or medial hinge plates 310, 350. As illustrated the lateral washer 320 includes a proximal aperture 344a, a distal aperture 344b, an anterior aperture 346a, and a posterior aperture 356b. In some embodiments, the lateral washer 320 may be constructed of a material having a low coefficient of friction, such as plastic. The lateral washer 320 thus enables the proximal and distal arms 140a, 140b to rotate more easily within the hinge assembly 300. In some embodiments one or both of the lateral and/or medial washers 320, 340 can be omitted.

The proximal apertures 312a, 324a, 144a, 344a, 352a can be aligned along the proximal arm rotation axis 2a. The distal apertures 312b, 324b, 144b, 344b, 352b can be aligned along the distal arm rotation axis 2b. Proximal and distal fasteners, such as rivets 127a, 127b can be used to secure the components of the hinge mechanism 300 as shown in the cross-sectional view of FIG. 15. The anterior apertures 314a, 326a, 346a, 354a can be aligned along the anterior adjustment axis 4a. The posterior apertures 314b, 326b, 346b, 354b can be aligned along the posterior adjustment axis 4b.

Figure 8A:
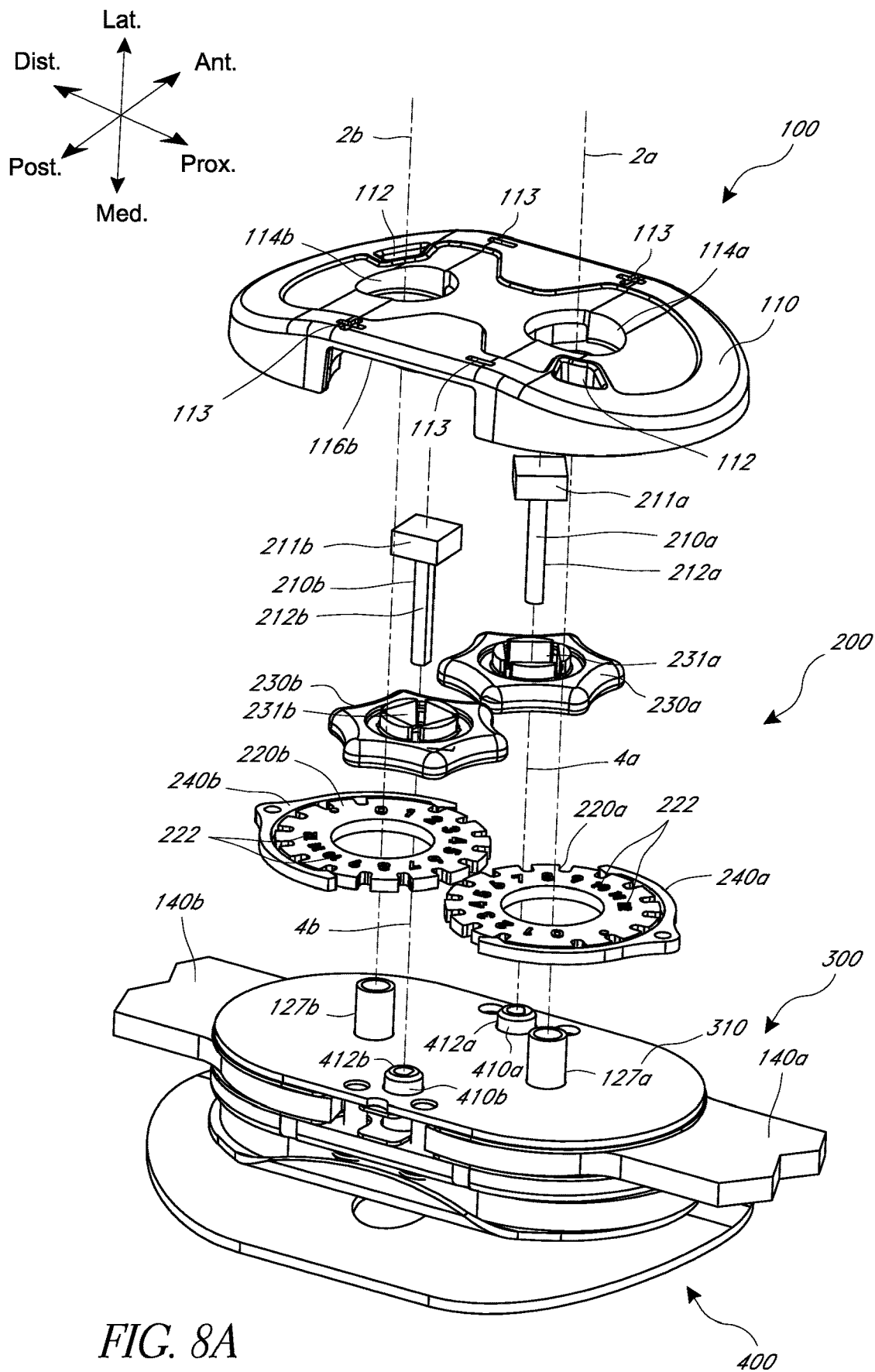
FIG. 8A is a partially exploded perspective view of an embodiment of an adjustment assembly for the hinge of FIG. 2A.

FIG. 8A is an exploded view of the adjustment assembly 200 and the cover 110. The hinge mechanism assembly 300 and the force application assembly 400 are also shown in FIG. 8A in an assembled state positioned below the adjustment assembly 200. In the illustrated embodiment, the adjustment assembly 200 includes the anterior drive key 210a, the anterior knob 230a, the anterior dial gear 220a, and the anterior pawl 240a. The adjustment assembly 200 also includes the posterior drive key 210b, the posterior knob 230b, the posterior dial gear 220b, and the posterior pawl 240b.

The anterior drive key 210a includes a keyed head 211a and a keyed shaft 212a. The keyed shaft 212a can extend through an opening in the anterior knob 230a. The keyed head 211a can be received in a corresponding keyed recess 231a in the anterior knob. In the illustrated embodiment, the keyed head 211a and the keyed recess 231a each comprise a square shape, although other shapes are possible. The keyed head 211a and the keyed recess 231a are configured such that when the keyed head 211a is received in the keyed recess 231a, rotation of the anterior knob 230a causes equal and corresponding rotation of the anterior drive key 210a. In other words, when assembled, the anterior knob 230a and the anterior drive key 210a rotate together. In some embodiments, the anterior knob 230a and the anterior drive key 211a may be formed as a unitary part.

The keyed shaft 212a of the anterior drive key 210a extends through the anterior knob 230a and into a keyed bore 412a of the anterior lead screw 410a. In the illustrated embodiment, the keyed shaft 212a comprises a D-bore shaft shape and the keyed bore comprises a corresponding D-bore shape, although other keyed shapes are possible. The keyed shaft 212a and the keyed bore 412a are configured to transfer rotation between the anterior drive key 210a and the anterior lead screw 410a. That is, the anterior drive key 210a and the anterior lead screw 410a rotate together. As will be described below, rotation of the anterior knob 230a is transmitted to the anterior lead screw 410a by the anterior drive key 210a causing lateral/medial displacement of an anterior portion of the force application assembly 400. The anterior drive key 211a, anterior knob 230a, and the anterior lead screw 410a are aligned along the anterior adjustment axis 4a.

As illustrated, in some embodiments, the anterior dial gear 220a and the anterior pawl 240a are associated with the anterior drive key 210a, anterior knob 230a, and the anterior lead screw 410a. As described herein, the anterior dial gear 220a can include position indicators 222 that are visible through a window 112 in the cover 110 to indicate the amount of displacement of the force application assembly 400. As will be described below, rotation of the anterior knob 230a may cause rotation of the anterior dial gear 220a, causing a different position indicator 222 to be visible. In some embodiments, the rotation of the anterior dial gear 220a is less than the rotation of the anterior knob 230a. For example, in some embodiments, a full rotation of the anterior knob 230a causes a partial rotation of the anterior dial gear 220a that corresponds to a change of one position indicator 222 on the anterior dial gear 220a. The anterior pawl 240a is engaged with the anterior dial gear 220a to limit or prevent inadvertent or unintentional rotation of the anterior dial gear 220a.

The posterior drive key 210b, posterior knob 230b, and posterior lead screw 410b are similarly configured to the corresponding anterior components described above, but are aligned along the posterior adjustment axis 4b. The posterior dial gear 220b and the posterior pawl 240b are associated with the posterior drive key 210b, posterior knob 230b, and posterior lead screw 410b and are similar to the corresponding anterior components described above.

Figure 8B:
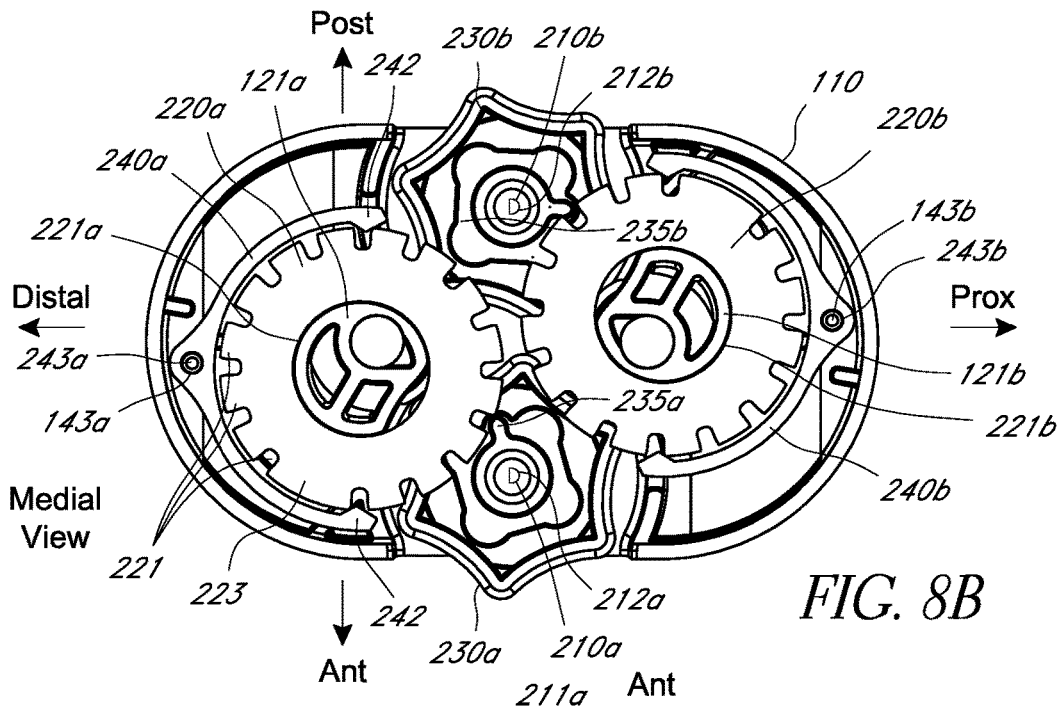
FIG. 8B is a medial view of some of the components of the adjustment assembly of FIG. 8A positioned within a cover of the hinge.
Figure 8C:
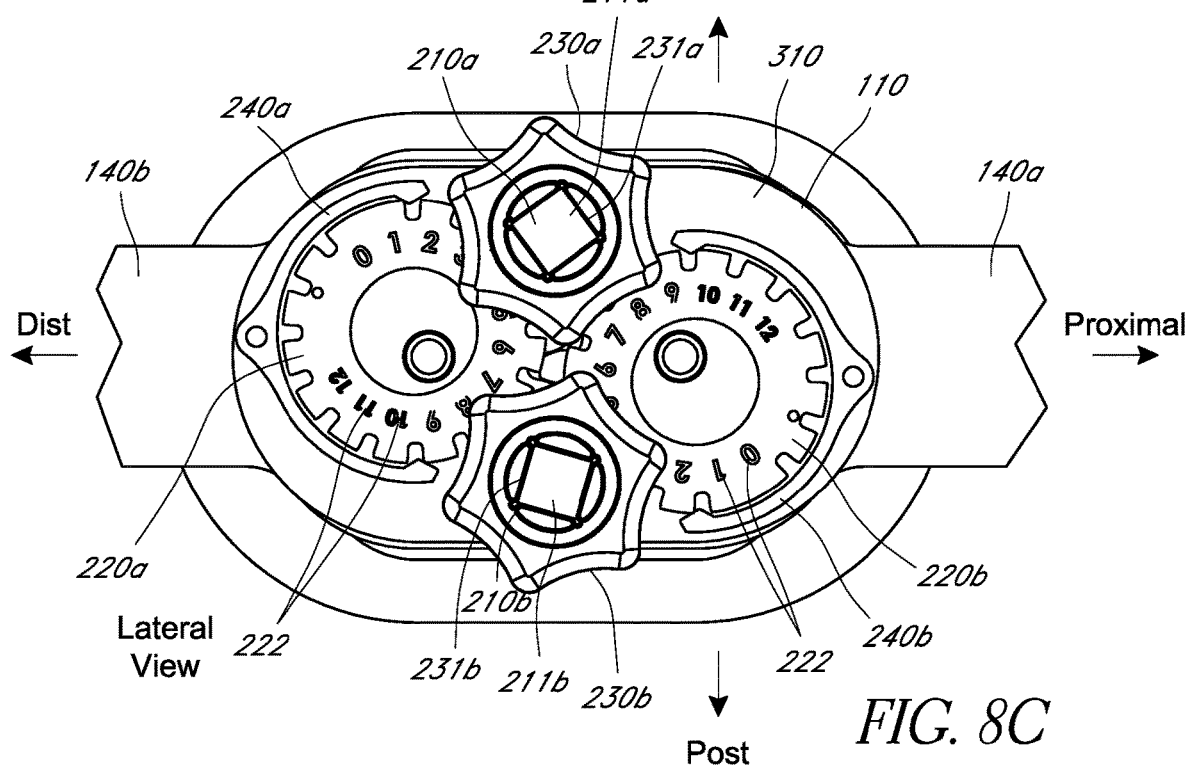
FIG. 8C is a lateral view of some of the components of the adjustment assembly of FIG. 8A with the cover removed.
Figure 9A:
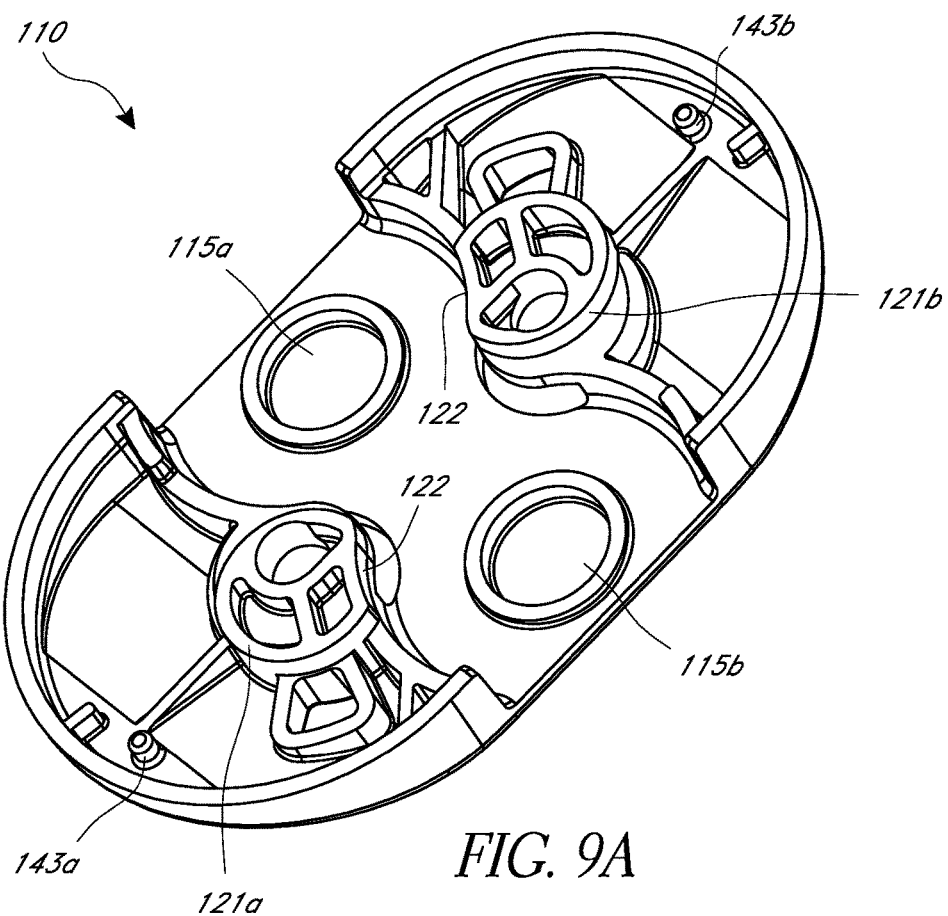
FIGS. 9A and 9B show medial perspective and medial views, respectively, of an embodiment of a cover for the hinge of FIG. 2A.
Figure 9B:
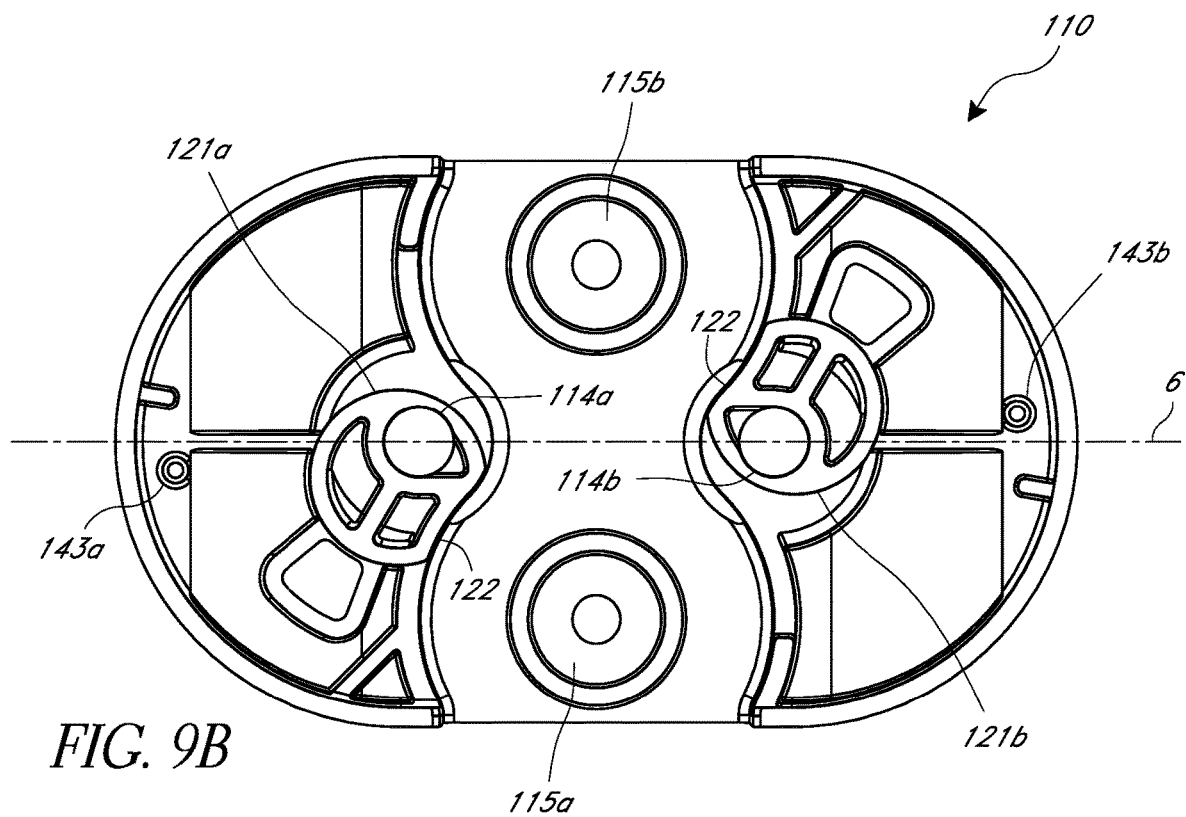

The interplay and arrangement of the components of the adjustment assembly 200 within the cover 110 will now be described with reference to the embodiment of FIGS. 8B-9B. FIG. 8B is a medial view of some of the components of the adjustment assembly 200 positioned within a cover 110. FIG. 8C is a lateral view of some of the components of the adjustment assembly 200 with the cover 110 removed. FIGS. 9A and 9B show medial perspective and medial views, respectively, of an embodiment of the cover 110.

As shown in FIG. 8A, the anterior dial gear 220a is a substantially annular gear having an internal aperture 221a. The internal aperture 221a is aligned with a central axis of the anterior dial gear 220a. The internal aperture 221a is positioned on an anterior boss 121a of the cover 110 (as seen in FIGS. 9A and 9B). In some embodiments, the anterior boss 121a extends from an inner surface of the cover 110. The anterior boss 121a and internal aperture 221a are configured such that the anterior dial gear 220a can rotate around the anterior boss 121a. In other words, the anterior dial gear 220a is received on and rotates around the anterior boss 121a of the cover 110.

The anterior dial gear 220a also includes a plurality of notches 221 spaced at even intervals around its perimeter. The notches are configured in size and shape to mesh with a tooth 235a that is formed on the medial surface of the anterior knob 230a during at least a portion of the rotation of the anterior knob 230a. For example, in the illustrated embodiment, during each full rotation of the anterior knob 230a, the tooth 235a engages with one of the notches 221 of the anterior dial gear 220a and causes a partial rotation of the anterior dial gear 220a that is equal to the distance between adjacent notches 221. In FIG. 8B, the tooth 235b of the posterior knob 230b is shown engaged with a notch 221 of the posterior dial gear 220b. In some embodiments, the anterior dial gear 240a includes a missing notch 223 (in other words, at one location around the perimeter of the dial gear 240a a notch is omitted or a spacing between two notches is larger (e.g., twice as large) as a spacing between the remaining notches). The missing notch 223 may serve to limit rotation of the anterior knob 230a. For example, as described above, for each rotation of the anterior knob 230a the tooth 235a advances the anterior dial gear 240a one notch. However, when the tooth 235a reaches the missing notch 223, the missing notch 223 prevents the anterior knob 230a from rotating further in that direction. The location of the missing notch 223 may be positioned to represent a maximum and/or minimum lateral/medial displacement of the force application assembly 400.

As shown in FIGS. 8B, 9A, and 9B, the anterior boss 121a of the cover 110 is offset toward the anterior side of the cover 110 from the central longitudinal axis 6 of the cover 110. This offset allows the anterior dial gear 220a to engage with the anterior knob 230a without interfering with the posterior knob 230b. Similarly, the posterior boss 121b is offset toward the posterior side of the cover to allow the posterior 220b to engage with the posterior knob 230b without interfering with the anterior knob 230a.

The anterior pawl 240a is configured to prevent rotation of the anterior dial gear 220a when the tooth 235a is not engaged with any notch of the anterior dial gear 220a. In FIG. 8B, the anterior knob 230a is illustrated in a rotational position where the tooth 235a is not engaged with any notch 221 of the anterior dial gear. In the illustrated embodiment, the anterior pawl 240a comprises a C-shape that partially surrounds the anterior dial gear 220a. Free ends 242 of the anterior pawl 240a are engaged with notches 221 to prevent or limit rotation. The C-shape of the anterior pawl 240a is configured to be flexible such that rotation of the dial gear 220a caused by the anterior knob 230a causes the free ends 242 to flex outward allowing the dial gear 220a to rotate. The anterior pawl 240a includes an aperture 243a that is mounted on a post 143a that extends from the interior surface of the cover 110 as shown in FIGS. 9A and 9B. Other shapes for the anterior pawl 240a are possible.

As shown in FIG. 8B, the keyed shaft 210a of the anterior drive key 210a extends through an opening in the anterior knob 230a.

Turning now to the lateral view of FIG. 8C, the anterior dial gear 220a and the anterior pawl 240a rest substantially on top of the lateral hinge plate 310. Accordingly, in some embodiments, the anterior dial gear 220a and the anterior pawl 240a are sandwiched between the lateral hinge plate 310 and the interior surface of the cover 110. The anterior dial gear 220a can include the series of position indicators 222 on the lateral surface thereof. As previously noted, the position indicators 222 specify the displacement of the force application assembly 400 from the hinge 100. The illustrated embodiment shows numbers one through twelve as the position indicators 222, but other indicators may be used, such as, colors or symbols.

As shown in FIG. 8C, the keyed head 211a of the anterior drive key 210 is received within the keyed recess 231a of the anterior knob 230a. In some embodiments, a portion of the anterior knob 230a is configured to rotate spaced laterally above the anterior dial gear 220a. In some embodiments, the tooth 235a of the anterior knob 230a is located on a medial protrusion that extends from the medial side of the anterior knob 230a. In some embodiments, the medial protrusions rests and rotates on the lateral hinge plate 310 and positions the tooth 235a in the plane of the anterior dial gear 220a and spaces the remainder of the anterior knob 230a above the anterior dial gear. As illustrated in FIGS. 9A and 9B, in some embodiments, interior surface of the cover 110 may include an anterior recess 115a. The anterior recess 115a may be configured to receive a portion of the anterior knob 230a to secure the anterior knob 230a. For example, in some embodiments, a lateral surface of the anterior knob 230a includes a shape that fits within the anterior recess 115a of the cover 110.

Although the preceding description of FIGS. 8B-9C has discussed the anterior components of the adjustment assembly 200, the posterior components of the adjustment assembly 200 may be similarly configured.

Returning to FIG. 8A, as illustrated, the cover 110 can comprise cover markings 113 on the anterior and posterior edges, two windows 112, a proximal and distal aperture 114a, 114b, and an anterior and posterior knob opening 116a, 116b, although other arrangement and features for the cover 110 are possible.

Figure 15:
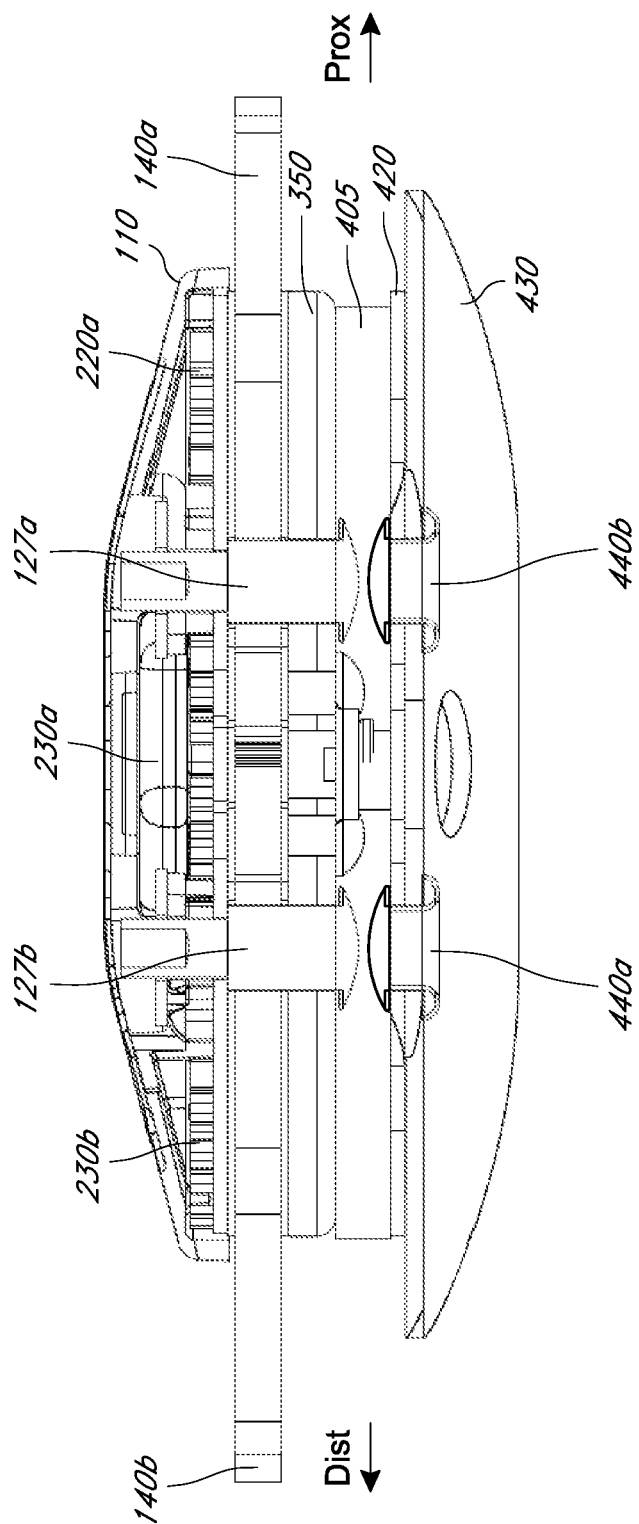
FIG. 15 is a cross-sectional view of the hinge taken along the line 15-15 shown in FIG. 2B.

The hinge mechanism assembly 300, the adjustment assembly 200, and the cover 110 may be secured together using fasteners, such as rivets 127a, 127b (see FIG. 8A and FIG. 15). The rivets 127a, 127b may extend along the proximal and distal rotation axes 2a, 2b.

Figure 10:
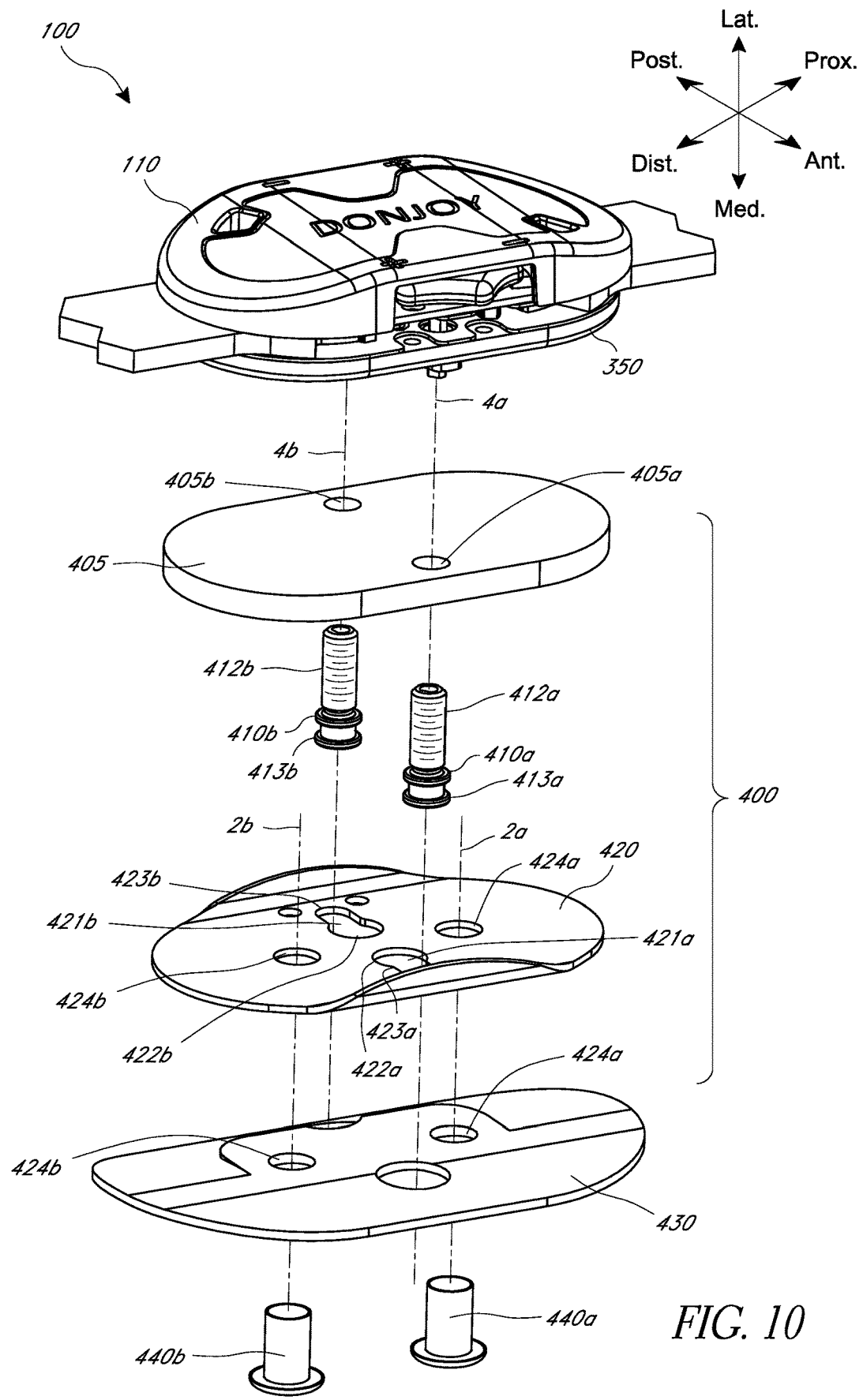
FIG. 10 shows a lateral partially exploded view of an embodiment of the force application assembly for the hinge of FIG. 2A.

FIG. 10 shows a lateral partially exploded view of an embodiment of the force application assembly 400. In the illustrated embodiment, the force application assembly includes a foam pad 405, the anterior and posterior lead screws 410a, 410b, a loading plate 420, and a condyle shell 430.

In some embodiments, the foam (or other cushioning material) pad 450 is preferably made of foam or other suitable material for padding. The foam pad 450 is the substantially similar to the oval and flat shape of the medial hinge plate 350. In some embodiments, the foam pad 450 may be approximately 2 mm thick, although other thicknesses are possible. The foam pad 450 is positioned between the medial hinge plate 350 and loading plate 420. The foam pad 450 has an anterior and posterior aperture 405a, 405b corresponding to the anterior and posterior apertures 352a, 352b of the lateral and medial hinge plates 310, 350. The anterior and posterior apertures 405a, 405b of the foam pad 450 allow the threaded lateral ends 412a, 412b of the lead screws 410a, 410b to extend there through.

In some embodiments, the loading plate 420 may be substantially oval shaped and can include proximal and distal apertures 424a, 424b corresponding to the proximal and distal apertures 352a, 352b of the hinge plates 310, 350. In the illustrated embodiment, the posterior and anterior edges of the loading plate 420 are curved in the lateral direction. The loading plate 420 also can include anterior and posterior slots 421a, 421b that are aligned with the anterior and posterior apertures 405a, 405b of the foam pad 500 along the anterior and posterior adjustment axes 4a, 4b. The anterior and posterior slots 421a, 421b may extend in the anterior/posterior direction and may be located near the center of the loading plate 420 as measured in the proximal/distal direction. The anterior and posterior slots 421a, 421b can include a narrow portion at the posterior end 423b and a narrow portion at an anterior end 422b. The loading plate 420 also includes an anterior slot 421a is substantially identical to the posterior slot 421b, but is a mirror image of the posterior slot 421b about a line bisecting the loading plate 420 in a proximal/distal direction. The anterior slot 421a receives a medial end 411a of the anterior lead screw 410a. The posterior slot 421b receives a medial end 411b of the posterior lead screw 410b.

In some embodiments, the condyle shell 430 is also substantially oval shaped and includes proximal and distal apertures 424a, 424b corresponding to the proximal and distal apertures of the loading plate. In the illustrated embodiment, the posterior and anterior edges are curved in the posterior direction. A medial surface of the loading plate 420 is secured to a lateral surface of the condyle shell 430. The loading plate 420 is secured to the condyle shell 430 via a pair of rivets 440a, 440b (see FIGS. 10 and 14) that cooperate with the proximal and distal apertures 424a, 424b on the loading plate 420 and condyle shell 430. However, other suitable methods could be used to secure the loading plate 420 and condyle shell 430.

Figure 11A:
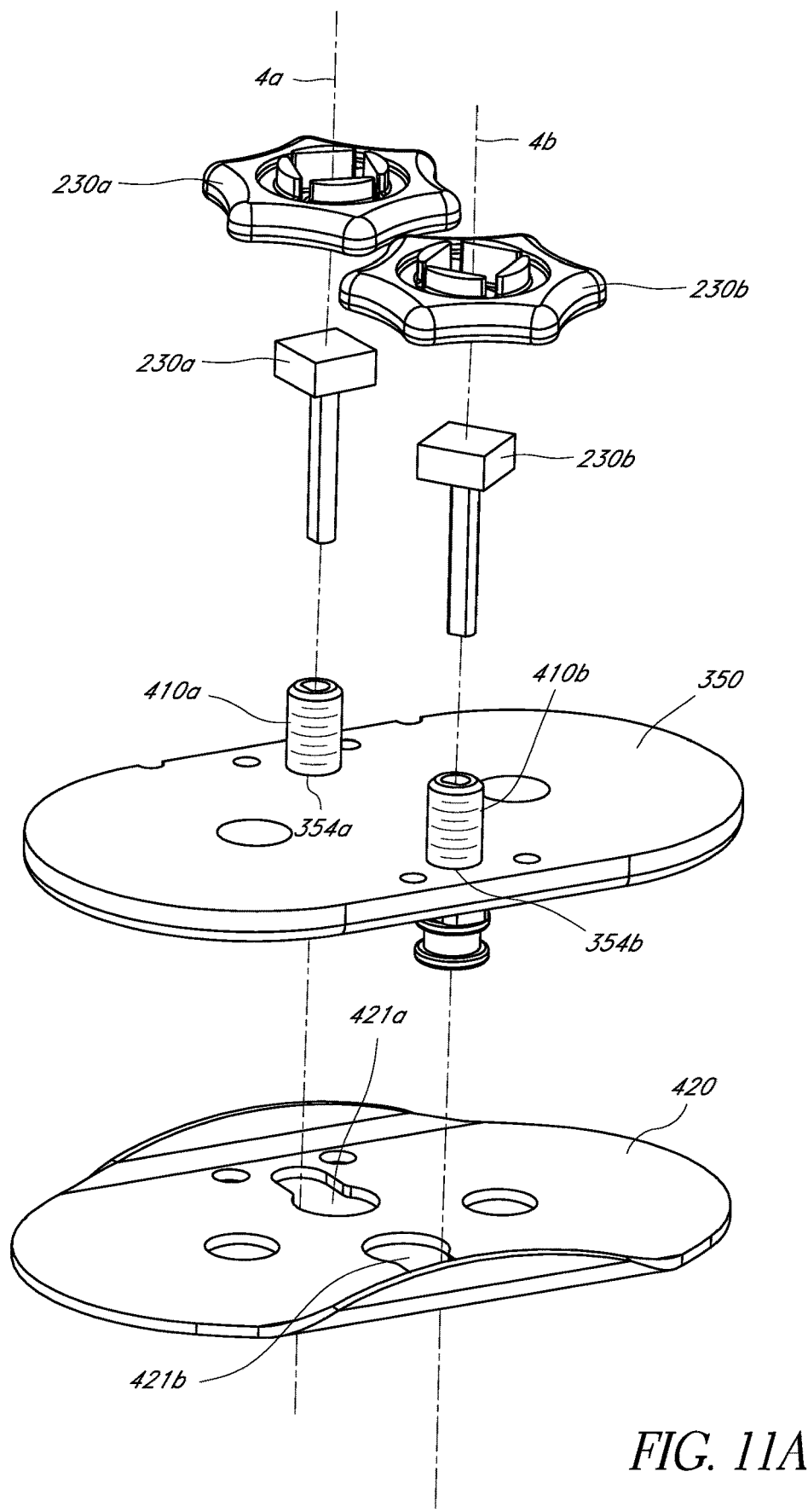
FIGS. 11A and 11B show lateral and medial exploded perspective views, respectively, of some of the components of the adjustment assembly of FIG. 8A.
Figure 11B:
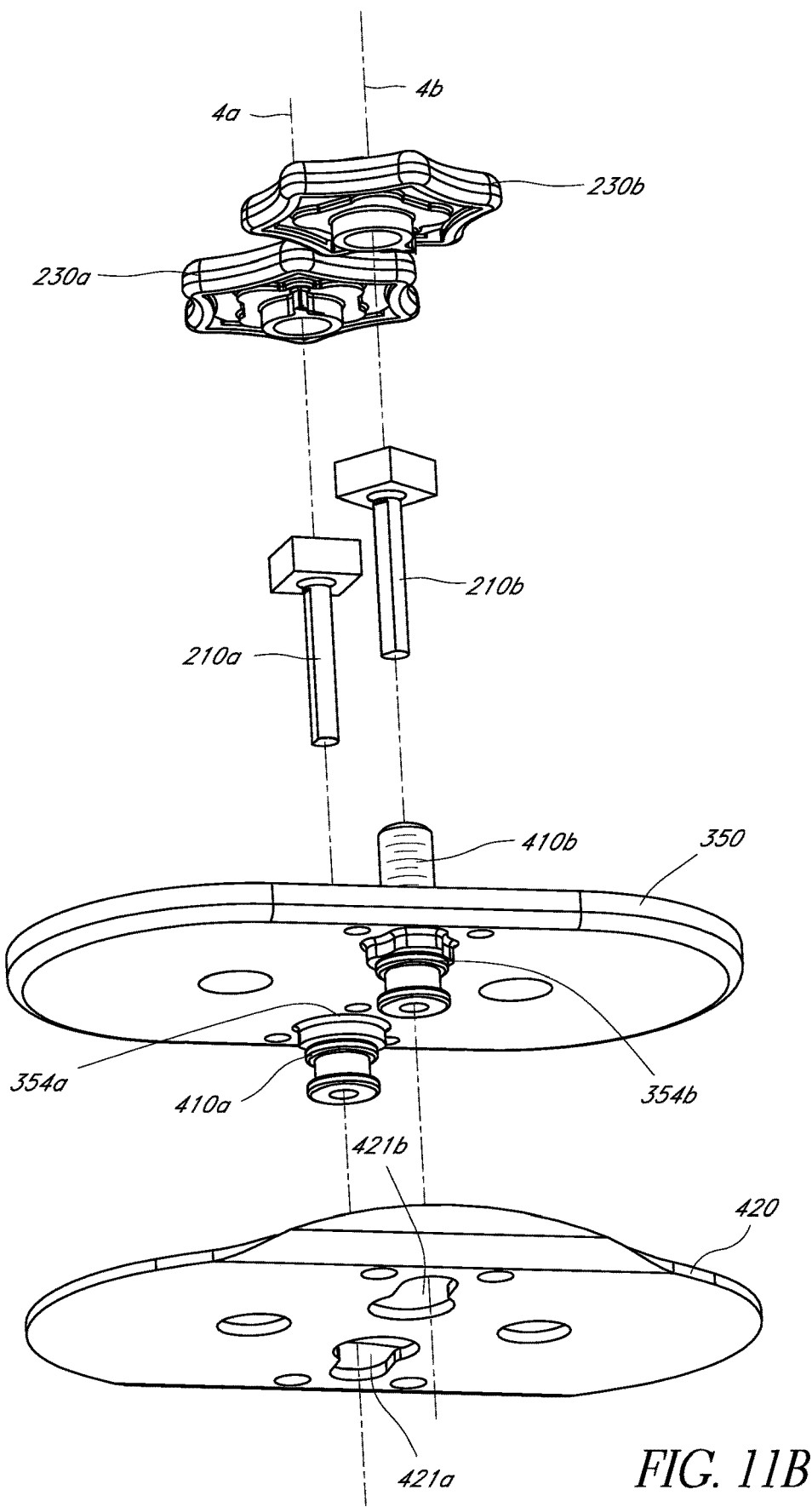

FIGS. 11A and 11B show lateral and medial exploded perspective views of the components of the hinge 100 that allow for lateral/medial displacement of the force application assembly 100 according to one embodiment. As discussed previously, rotation of the anterior knob 230a is transmitted to the lead anterior lead screw 410a by the anterior drive key 410a. The anterior lead screw 410a is externally threaded and received in the internally threaded anterior aperture of the medial hinge plate 350. As the anterior lead screw 410a rotates, the threaded engagement between the anterior lead screw 410a and the medial hinge plate 310 causes the anterior lead screw 410 to telescope in and out (medially and laterally) relative to the medial hinge plate 350. The anterior lead screw 410a slides along the keyed shaft 212a of the anterior drive key 210a. The medial end of the anterior lead screw 410a is received in the anterior slot 421a of the loading plate 420. Thus, as the anterior lead screw 410a telescopes in and out, the anterior portion of the loading plate 420 is displaced in a lateral/medial direction. The posterior portion of the loading plate 420 is similarly displaceable by rotation of the posterior knob 430b.

Figure 12:
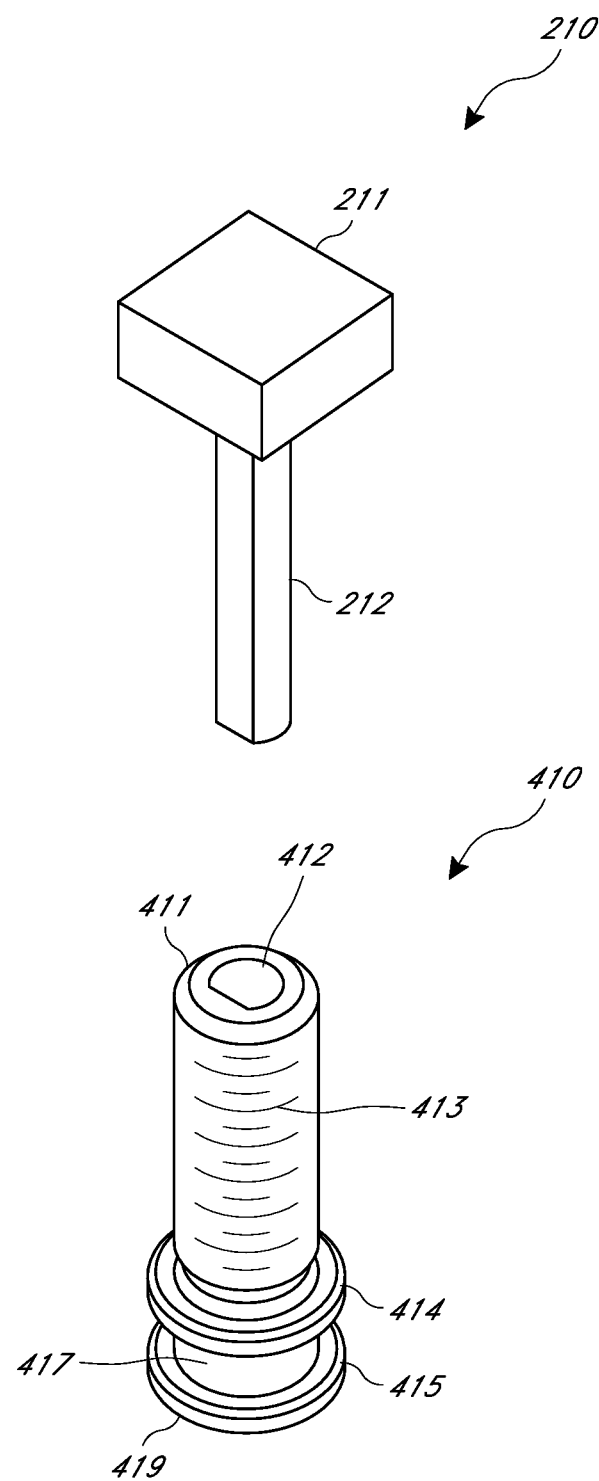
FIG. 12 shows a perspective view of an embodiment of a drive key and an adjustment screw.

FIG. 12 shows a detailed perspective view of an embodiment of a drive key 210 and a lead screw 410. As described above, the drive key 210 includes a keyed head 211 and a keyed shaft 212. In the illustrated embodiment, the lead screw 410 includes an externally threaded portion 413 and the keyed bore 412, which extends into a lateral end of the lead screw 410. The medial end 419 of the lead screw 410 includes a first coaxial disk 414 having a diameter larger than that of the threaded portion 412. The medial end 419 also includes a second coaxial disk 415 that is separated from the first coaxial disk 414 by a coaxial cylindrical portion 416 having a diameter substantially the same as the threaded portion 413. A space between the two disks 414, 415 thus defines an annular gap 417. The two disks 414, 415 and the annular gap 417 are used to secure the medial end 419 of the lead screw 410 to the loading plate 420.

Figure 13B:
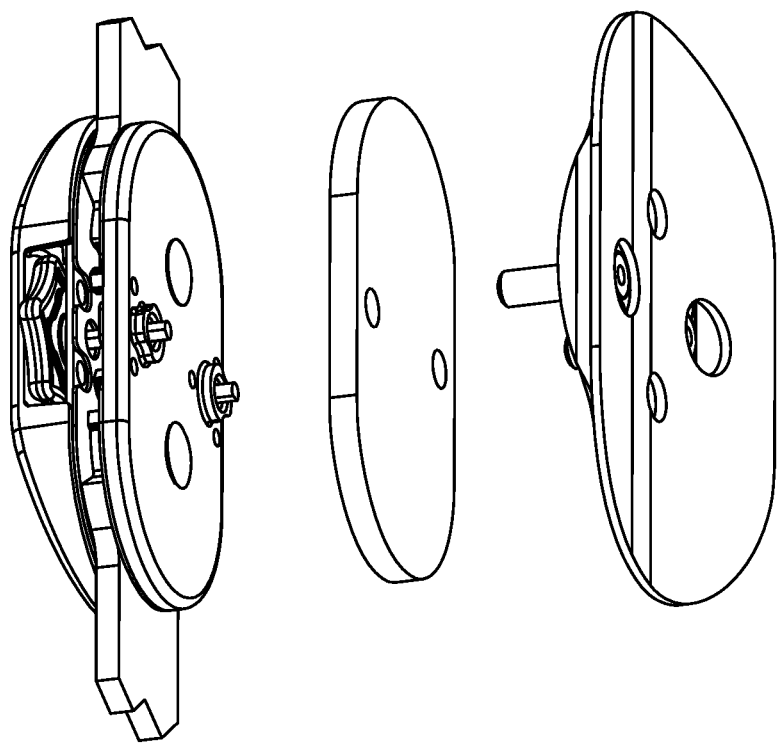
FIGS. 13A and 13B shows lateral and medial partially exploded perspective views, respectively, of the hinge of FIG. 2A.
Figure 13A:
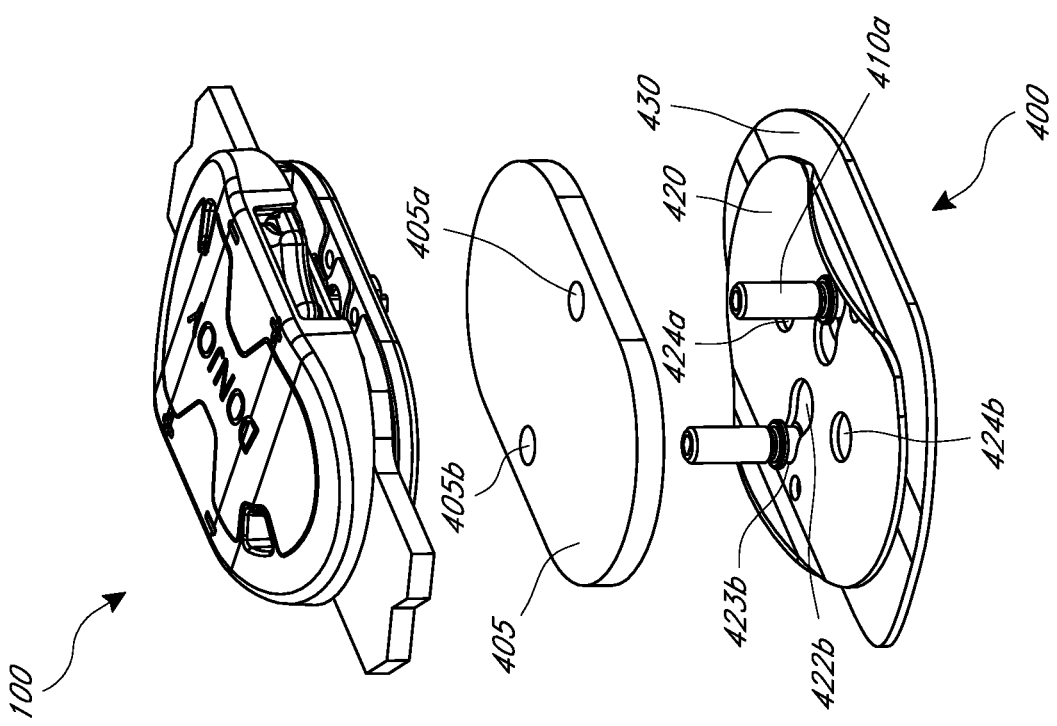

FIGS. 13A and 13B show lateral and medial partially exploded perspective views, respectively, of the hinge 100 according to one embodiment. As shown in FIGS. 13A and 13B, the gap 417a of the anterior lead screw 410a engages the anterior slot 421a on the loading plate 420, and the gap 417b on the posterior lead screw 410b engages the posterior slot 421b of the loading plate 420. The disks 414, 415 at the medial ends 419 of the lead screws 410a, 410b each have a smaller diameter than a width of the wide portions of the anterior and posterior slots 421a, 421b. However, the disks 414, 415 each have a larger diameter than a width of the narrow portions of the anterior and posterior slots 423a, 423b. Further, the cylindrical portions 416a, 416b of each lead screw 410a, 410b between the disks 414, 415 have smaller diameter than the width of the narrow portions 423a, 423b of the anterior and posterior slots 421a, 421b. Thus, the anterior lead screw 410a is insertable within the wide portion 422a of the anterior slot 421a and slidable into the narrow portion 423a of the anterior slot 421a are disposed between the disks 414, 415, such that there is a small amount of "play" between the loading plate 420 and the lead screws 410a, 410b. The posterior lead screw 410b is engageable with the posterior slot 421b in the same manner that the anterior lead screw 410a is engageable with the anterior slot 421a.

Figure 14:
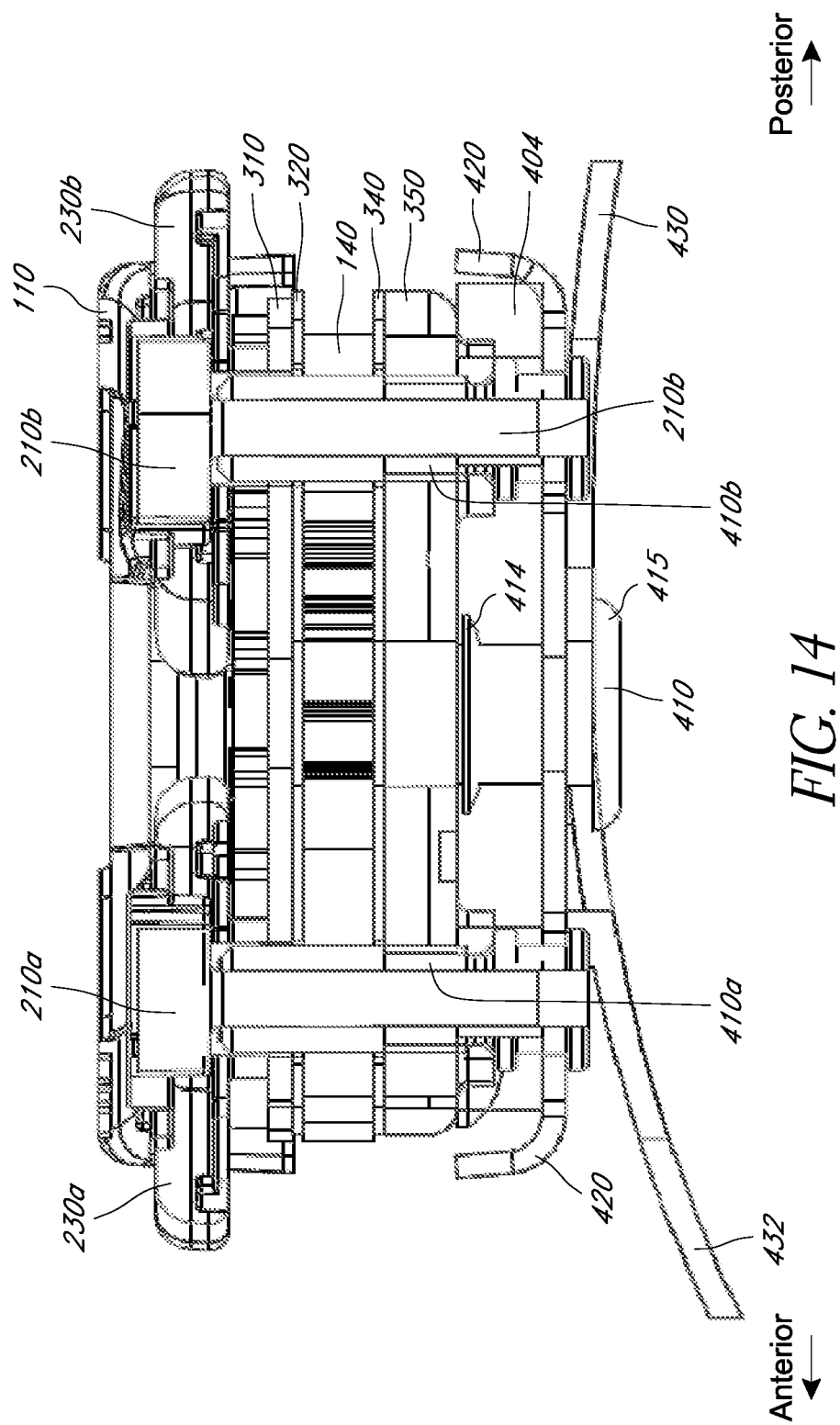
FIG. 14 is a cross-sectional view of the hinge taken along the line 14-14 shown in FIG. 2B.

FIG. 14 is a cross-sectional view of the hinge taken along the line 14-14 shown in FIG. 2B. FIG. 15 is a cross-sectional view of the hinge taken along the line 15-15 shown in FIG. 2B.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A hinge comprising:
   a first arm;
   a second arm;
   a hinge plate, the first arm connected to the hinge plate for rotation about a first axis and the second arm connected to the hinge plate for rotation about a second axis, the hinge plate including an internally threaded aperture;
   a force application assembly;
   an adjustment assembly including
   an externally threaded lead screw engaged with the internally threaded aperture of the hinge plate and having
   a medial end connected to the force application assembly, and
   a keyed bore extending along a longitudinal axis of the externally threaded lead screw from a lateral end of the externally threaded lead screw toward the medial end,
   a drive key having a keyed shaft slidingly engaged with the keyed bore,
   a knob connected to a lateral end of the drive key such that rotation of the knob causes rotation of the drive key which causes rotation of the externally threaded lead screw through engagement of the keyed shaft and the keyed bore, wherein the rotation of the externally threaded lead screw causes the externally threaded lead screw to move laterally or medially along the longitudinal axis relative to the hinge plate and the drive key to cause lateral or medial displacement of the force application assembly, and wherein the keyed bore slides laterally or medially along keyed shaft of the drive key as the keyed bore and the keyed shaft rotate together, and
   a cover having an opening positioned on an anterior side or a posterior side of the cover, wherein the knob and drive key are positioned between the cover and the hinge plate, and wherein the knob extends at least partially through the opening.

2. The hinge of claim 1, the adjustment assembly further comprising:
   a dial gear comprising a plurality of notches; and
   a tooth extending from the knob that engages with the plurality of notches during at least a portion of a full rotation of the knob such that rotation of the knob causes rotation of the dial gear.

3. The hinge of claim 2, the adjustment assembly further comprising a pawl having a free end that engages with the plurality of notches of the dial gear.

4. The hinge of claim 3, wherein the pawl is configured to prevent rotation of the dial gear when the tooth of the knob and the notches of the dial gear are not engaged.

5. The hinge of claim 2, the dial gear comprises a missing notch that limits rotation of the knob.

6. The hinge of claim 2, wherein a boss extends from an interior surface of the cover, and wherein the dial gear is mounted on and rotates around the boss.

7. The hinge of claim 1, further comprising a spacer between the force application assembly and the hinge plate, the externally threaded lead screw extending through an aperture in the spacer.

8. The hinge of claim 7, wherein the spacer comprises foam.

9. The hinge of claim 1, wherein the hinge plate comprises a medial hinge plate, the hinge further comprising:
   a lateral hinge plate, the first and second arms positioned between the lateral hinge plate and the medial hinge plate.

10. The hinge of claim 9, wherein the keyed shaft of the drive key extends through an aperture in the lateral hinge plate.

11. The hinge of claim 1, wherein rotation of the knob causes lateral or medial displacement of the externally threaded lead screw through the internally threaded aperture of the hinge plate.

12. The hinge of claim 1, wherein the keyed bore of the externally threaded lead screw comprises a D-bore shape and the keyed shaft of the drive key comprises a D-bore shape.

13. The hinge of claim 1, wherein the force application assembly comprises:
   a loading plate connected to the medial end of the externally threaded lead screw; and
   a condyle shell.

\* \* \* \* \*